United States Patent [19]
Josephson et al.

[11] Patent Number: 5,981,507
[45] Date of Patent: Nov. 9, 1999

[54] POLYMERIC CARRIERS LINKED TO NUCLEOTIDE ANALOGUES VIA A PHOSPHORAMIDE BOND

[75] Inventors: Lee Josephson, Arlington; Ernest V. Groman, Brookline; Yong-Qian Wu, Southboro, all of Mass.

[73] Assignee: Advanced Magnetics, Inc., Cambridge, Mass.

[21] Appl. No.: 08/766,597

[22] Filed: Dec. 12, 1996

Related U.S. Application Data

[60] Provisional application No. 60/027,325, Oct. 3, 1996, provisional application No. 60/028,331, Oct. 11, 1996, and provisional application No. 60/008,600, Dec. 14, 1995.

[51] Int. Cl.$^6$ .................................................. A01N 43/04
[52] U.S. Cl. ............................... 514/48; 514/45; 514/49; 514/51
[58] Field of Search ............................ 424/488, 493, 424/497; 435/89, 101

[56] References Cited

U.S. PATENT DOCUMENTS

| | | | |
|---|---|---|---|
| 3,284,440 | 11/1966 | Patchett et al. | 260/211.5 |
| 4,046,722 | 9/1977 | Rowland | 260/6 |
| 4,064,118 | 12/1977 | Wong | 260/112.5 |
| 4,211,771 | 7/1980 | Witkowski | 424/180 |
| 4,698,387 | 10/1987 | Schmidt et al. | 525/54.1 |
| 5,149,794 | 9/1992 | Yatvin et al. | 536/29 |
| 5,233,031 | 8/1993 | Borch et al. | 536/28.53 |
| 5,336,506 | 8/1994 | Josephson et al. | 424/488 |
| 5,349,052 | 9/1994 | Delgado et al. | 530/351 |
| 5,424,297 | 6/1995 | Rubio et al. | 514/46 |
| 5,490,991 | 2/1996 | Enriquez et al. | 424/488 |
| 5,554,386 | 9/1996 | Groman et al. | 424/488 |

FOREIGN PATENT DOCUMENTS

| | | | |
|---|---|---|---|
| 1 541 436 | 2/1976 | United Kingdom | C07G 7/00 |
| WO 90/05736 | 5/1990 | WIPO | C07H 19/00 |
| WO 90/10012 | 9/1990 | WIPO | C07H 19/10 |
| 95/00177 | 1/1995 | WIPO | A61K 47/48 |
| WO 95/00177 | 1/1995 | WIPO | A61K 47/48 |
| 95/05199 | 2/1995 | WIPO | A61K 47/48 |
| 95/18636 | 7/1995 | WIPO | A61K 47/48 |

OTHER PUBLICATIONS

Srinivas et al., 1993, Antimicrob. Agents Chemo. 37:2247–2250.

Benet et al., 1990, "Pharmacokinetics: The Dynamics of Drug Absorption, Distribution, and Elimination", in Goodman and Gilman's The Pharmacological Basis of Therapeutics, Eigth edition, Goodman et al., eds., Pergamon Press Inc., New York, pp. 3–32.

*Primary Examiner*—Laurie Scheiner
*Assistant Examiner*—J. S. Parkin
*Attorney, Agent, or Firm*—Bromberg & Sunstein LLP

[57] ABSTRACT

Novel compositions of nucleotide analog prodrugs for the treatment of viral infections and cancer are herein disclosed. The prodrugs have a biocompatible polymeric carrier conjugated to the nucleotide analog via an amino-phosphate linkage. The amino group is provided by the carrier, which either inherently possesses a primary amine, or is modified with reactive groups that incorporate the primary amine onto the carrier. The carrier can be a polyamino acid, a polyvinylic polymer, a polysaccharide or combinations thereof, such as polylysine, HPMA, dextran, hydroxyethyl starch, or polyethylene glycol; the nucleotide analog can be ribavirin araA, AZT, acyclovir, 5-FUDR, araC or ddI. Methods of treating a viral infection of cancer using these prodrugs are also disclosed. The prodrugs endow the nucleotide analogs with substantially enhanced therapeutic efficacy and reduces toxicity in comparison to the nucleotide analog alone.

29 Claims, 5 Drawing Sheets

POLYMERIC CARRIERS LINKED TO NUCLEOTIDE ANALOGUES VIA A PHOSPHORAMIDE BOND

CROSS REFERENCE TO RELATED APPLICATIONS

This application claims priority from Provisional Application Serial No. 60/027,325 filed Oct. 3, 1996, Provisional Application Serial No. 60/028,331 filed Oct. 11, 1996, and Provisional Application Serial No. 60/008,600 filed Dec. 14, 1995 all of which are incorporated herein by reference.

FIELD OF THE INVENTION

This invention relates to the synthesis of macromolecular prodrugs of nucleotide analogs and their uses as antiviral and anticancer agents.

BACKGROUND

Nucleoside analogs are a class of compounds that have been shown to exert antiviral and antitumor activity both in vitro and in vivo, and thus, have been the subject of widespread research for the treatment of viral infections and cancer. Nucleoside analogs are molecules that antagonize or mimic the action of naturally occurring nucleosides. In general, nucleoside analogs consist of purine, pyrimidine or similar heterocyclic derivatives of adenine, cytosine, thymine, or guanine, and a glycoside or glycoside analog structure. Examples of nucleoside analogs include, but are not limited to, acyclovir, ribavirin, 3TC, AZT, araC, araA, DAPD ((−)-β-D-2,6-diaminopurine dioxalane) and 5-FUDR. Several of these compounds are shown below.

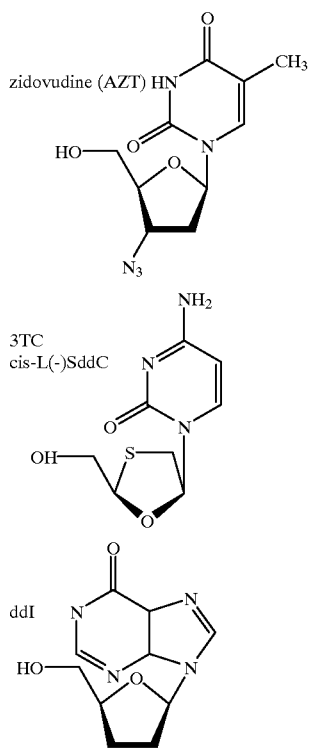

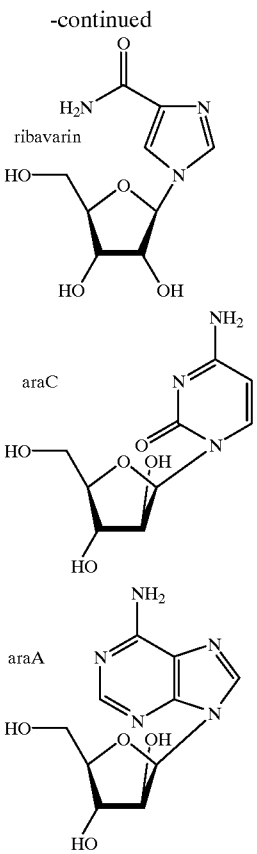

Nucleoside analogs are therapeutically inactive compounds and are converted by host or viral enzymes to their respective active anti-metabolites, which, in turn, inhibit polymerases involved in viral or cell proliferation. The activation occurs by a variety of mechanisms, such as the addition of one or more phosphate groups and, or in combination with, other metabolic processes. For example, in the cell, the inosine of ddI is converted to adenine (ddA) and phosphate groups are then added to yield the active antimetabolite ddATP.

Nucleoside analogs suffer from a variety of problems that limits their use in antiviral therapy.

1. Poor Solubility and Cell Penetration

Nucleoside analogs must be able to penetrate cell membranes and gain access to the intracellular space to be effective as therapeutics. Some nucleoside analogs traverse cell membranes by diffusional processes, which are governed by the charge and lipophilicity of the molecule. Others enter the cell by interaction with transporters for nucleosides present in the cell membrane. However, some nucleoside analogs exhibit poor membrane permeability and are poorly soluble in water, thus, limiting their ability to penetrate cells.

2. Attack by Deaminases

A second problem associated with nucleosides analogs having an amine group on the base (i.e., adenine or cytosine) is deamination by host deaminases. For example, deaminases convert araA into arahypoxanthine, which has little antiviral effect.

3. Dependence on Host or Viral Enzymes for Phosphorylation

Nucleoside analogs are dependent on host or viral enzymes for the phosphorylation into the active anti-metabolites to occur. In the absence, or low activity of these enzymes, the nucleoside is poorly converted into the bioactive form.

Administration of the phosphorylated form, i.e., the nucleotide analog, could bypass one or more of the phosphorylation steps performed by the cell, a step in the conversion of the nucleoside into the bioactive form. In addition, nucleotide analogs are structurally and metabolically closer to the therapeutically active phosphorylated form(s). However, the phosphate group is highly charged, which makes the nucleotide analog less membrane-permeable than the nucleoside analog. Secondly, host enzymes, such as phosphatases, hydrolyze the nucleotide analog back to the nucleoside analog, which then must undergo re-phosphorylation. For these reasons, nucleotide analogs are little used in pharmacology.

4. Toxic Effects

When administered to patients, nucleoside analogs have shown toxicity to liver, bone marrow, and the nervous system. In the case of antiviral therapy, nucleoside analogs have been rarely curative, and the side effects that arise during chronic administration of the drug often cause therapy to be discontinued or altered. In the case of cancer therapy, where intent is to kill the cancer cells, the compound and protocol (dose, method of administration, timing of doses) must be carefully designed and monitored to minimize the damage to non-cancerous tissues.

The following various approaches have been attempted to overcome the membrane permeability problem and improve the therapeutic efficacy of the nucleotide analog with limited success.

Low Molecular Weight Prodrugs

Prodrugs of nucleotide analogs are inactive forms of the nucleotide analog which are converted in vivo into the bioactive form. Low molecular weight prodrugs (molecular weights below 5 kilodaltons) consist of various low molecular weight groups reacted with the oxygen atoms of the phosphate group at the 5' OH position. These low molecular weight groups obscure or eliminate the charged oxygen atoms of the phosphate group, thereby allowing cell uptake to occur. (Lefebvre I, et al. J. Med Chem, 1995; 38:3941–3950, incorporated herein by reference). Once inside the cell, these multiple groups must be removed before any antiviral activity is achieved. McGuigan (McGuigan et al, WO 90/05736 Publ. Nov. 23, 1898) synthesized a series of prodrugs of AZT substituted with di and tri ester phosphonate alkyl chains (C1–C18). However, these derivatives were poorly active.

Different Types of Linkages between the Phosphate and the Nucleoside Analog

Phosphonate nucleotide analog prodrugs have a phosphorus atom (—P—) firmly attached to the glycoside portion of the nucleoside analog by a —P—C— linkage rather than with a —P—O—C— diester linkage. Though stable to phosphatases, phosphonate nucleotide analogs are highly charged, poorly absorbed after oral administration, and are poorly membrane permeable. Depending on the linking groups used, the cleavage of the —P—C— linkage can produce toxic intermediates (Krise et al (Krise J P, Stella V. J., Prodrugs of phosphates, phosphonates and phosphinates, Advanced Drug Delivery Reviews, 1996, 19:287–310, incorporated herein by reference).

Receptor Directed Nucleotide Conjugates

Enriquez et al., (U.S. Pat. No. 5,490,991) overcame the membrane permeability problem by coupling nucleotide analogs to molecules recognized by certain receptors. These conjugates were selectively delivered to and internalized by cells bearing the particular receptor. Such conjugates concentrate the drug in receptor positive cells, for example hepatocytes in the liver, and limit its concentration, and toxic effects in non-receptor bearing cells. (Enriquez et al Bioconjugate Chemistry, 1995, 6:195–202.) However, they are limited by the requirement for a receptor on the cell surface. If a pathogen, e.g. virus, is not confined to receptor positive cells, receptor targeting can have limited effectiveness. Furthermore, certain neoplastic cells can lose receptors upon transformation, and cannot internalize the prodrug.

Polymeric Conjugates

High molecular weight polymers have been attached to nucleoside analogs as an attempt to improve the plasma stability and reduce the toxicity of the nucleoside analog. For example, when natural or synthetic polymers are linked to nucleoside analogs via chemically unstable linkages, such as esters, the linkage is subject to hydrolysis in the plasma, resulting in extracellular the release of the nucleoside analog. After release, the nucleoside is subject to enzymatic degradation in the blood as discussed previously. When Usher et al. (PCT WO 95/00177) coupled dextran to AZT, the conjugate was significantly less effective than the unconjugated AZT.

When highly chemically stable linkages between the polymer and the nucleoside analog are used (e.g., ether linkages), the drug may never be released. Instead, the conjugate can be excreted intact or stored for a long period of time, which can lead to toxicity.

Lipid Carrier Conjugates

Yarvin et al (U.S. Pat. No. 5,149,794) attached various antiviral and antineoplastic agents to lipid carrier in an attempt to enhance the rate at which these agents cross the cell membrane. However, these hydrophobic molecules tend to form micelles, which are rapidly cleared by the liver.

The prodrugs of nucleotide analogs that have been prepared to date lack a combination of plasma stability, intracellular lability (releasability) and therapeutic efficacy. Hence, there is a need for prodrugs of nucleotide analogs that are stable in plasma after administration, are capable of traversing cell membranes and releasing a therapeutically available form of the nucleotide analog intracellularly. There is a need furthermore for prodrugs that are capable of treating viral or cancer based diseases with therapeutic efficacy and reduced toxicity.

SUMMARY OF INVENTION

This invention is directed to novel compositions of antiviral and anticancer agents, specifically to prodrugs of nucleotide analogs. The prodrugs are characterized as having a macromolecular biocompatible polymeric carrier conjugated to the nucleotide analog via an amino-phosphate linkage. In one embodiment, the carrier may be conjugated directly to the nucleotide, provided that the carrier has a constituent primary amine for reacting with a phosphate on the nucleotide. The carrier can be, for example, a polyacrylamide, polyamino acid, preferably, polylysine.

In another embodiment, the carrier lacks the primary amine group and is conjugated to the nucleotide through a linking group that provides the primary amine for the carrier. The carrier can be a polysaccharide, polyvinylic polymer, or combinations thereof, for example polyglutamate or polyaspartate; the linking group can be lysine, polylysine, ornithine, polyornithine, or preferably a diamine, more preferably, 4-aminophenylalkylamine, jeffamine, butane diamine, hexane diamine, most preferably, ethylene diamine.

In another embodiment, the carrier may require a bridging group for coupling the linking group to the carrier. The carrier may be a polysaccharide, polyvinylic polymer, and combinations thereof, that contain at least one hydroxyl group, such as polyvinylpyrollidone, poly(oxyethylene) glycol (PEG), maleic anhydride divinylether (DIVMA), cellulose, and more preferably, pullulans, inulin, polyvinyl alcohol (PVA), N-(2-hydroxypropyl)methacrylamide (HPMA), and most preferably dextran and hydroxyethyl starch (HES). The bridging group can consist of oxygen containing groups such as straight chain acyl groups of $C_{2-10}$, (including ketones, aldehydes, esters, acids, ethers), substituted amides (e.g., imidocarbonate), alcohols or combinations thereof, preferably, carboxymethyl group (—CH$_2$CO—), or an isopropyl alcohol (—CH$_2$(CHOH)(CH$_2$)—) group.

In the above embodiments the nucleotide analog can be, for example, the mono-, di- or triphosphate form of ddI, AZT, and 5 FUDR, acyclovir, ribavirin, or ganciclovir, preferably araA, or araC.

Another embodiment of the invention provides for methods of treating a viral infection or cancer by providing a pharmaceutical composition of an anticancer or antiviral agent associated with a carrier via an amino-phosphate linkage between the carrier and the agent and administering the composition.

Another embodiment is directed to methods of endowing an antiviral agent with substantially enhanced therapeutic efficacy and reduced toxicity by conjugating the antiviral agent with a polymeric carrier via an amide-phosphate bond so as to reduce the cytotoxicity of conjugate in comparison to the antiviral agent alone.

DESCRIPTION OF THE FIGURES

FIG. 1 shows example structures of selected prodrugs of the invention.

DETAILED DESCRIPTION OF THE INVENTION

Figure 1A:
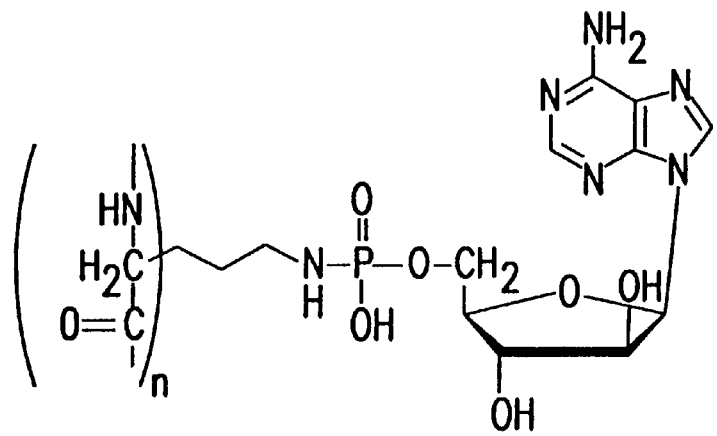
FIG. 1A shows the macromolecular carrier poly-L-lysine coupled to the nucleotide of araA (P-araA).

The invention provides for prodrugs of nucleotide analogs that are capable of effectively suppressing or inhibiting viral replication and proliferation of tumor cells. These prodrug compositions are stable in plasma, can traverse cell membranes and once inside cells, can be modified in such a way as to become therapeutically active. Further, these compositions exhibit reduced toxicity and increased efficacy over the parent nucleoside.

The compositions are represented by the general formula:

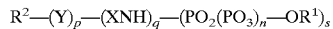

where:
R$^2$ is a macromolecular carrier having a primary amine group when p=0 and q=0
Y is a bridging group;
XNH is linking group;
OR$^1$ is a nucleoside analog;
PO$_2$—(PO$_3$)$_n$—OR$^1$ is a nucleotide analog (phosphorylated nucleoside analog), p≧q≧s≧1, except when p=0, q=0, or when p=0;
n is 0, 1, or 2; wherein the values for p, q, s and n are given as a molar ratio relative to R$^2$.

These new compositions generally consist of the nucleotide analog (—PO$_2$—(PO$_3$)$_{0-2}$—OR$^1$) attached to various biocompatible, macromolecular polymeric carriers containing primary amine groups. A single phosphoramide bond (—NH—PO$_2$—) between the phosphate group at the 5' position of the sugar (or its equivalent, in the case of acyclic nucleoside analogs) and the primary amine on the carrier links the nucleotide analogs to the carriers. One oxygen on each phosphate group is charged or uncharged depending upon the pH and the pK$_a$ of the oxygen. Two of the oxygen atoms of each phosphate are left unreacted with other substituent groups.

The carrier R$^2$ is a biocompatible polymer that inherently contains or is derivatized to contain a primary amine group. The term "biocompatible polymer" here and in the accompanying claims refers to natural or synthetic polymers that can be injected or ingested, are physiologically inert, exhibit no antiviral or anticancer activity themselves, and, after cleavage from the nucleotide, are either degraded to innocuous components or excreted as intact polymers. Furthermore, these polymers are "receptor inert," that is, they do not interact with known cell receptors such as the receptors involved in receptor mediated endocytosis, for example, the asialoglycoprotein receptors of the hepatocytes. The selection of polymer for use as carrier allows the overall physical properties of the prodrug, such as blood half life and membrane permeability to be altered. When the molecular weight of the prodrug is less than about 40 kDa, it will undergo renal elimination and have short blood half-life. Prodrugs made with macromolecular carriers greater than 40 kDa can have a long blood half-life. Proteins are not preferred for use as macromolecular carriers in this invention because they possess a variety of amino acid side chains with varying chemical reactivities. Hence, a single type of linkage between the nucleotide and a protein is difficult to attain. Crosslinking between the amino residues of one protein molecule and the carboxyl residues of another is also a problem with protein based carriers. Protein based carriers have been shown to be immunogenic.

According to the invention, we have selected macromolecular polymeric carriers that interact with cells and organs by non-specific adsorptive mechanisms and/or by fluid phase pinocytosis rather than by binding specific cellular receptors. Accordingly, molecules like arabinogalactan, lactosaminated human serum albumin, and galactosylated polylysine, which bind receptors endocytosing macromolecules (RME receptors), are not included here as macromolecular carriers.

In one embodiment, $R^2$ can be a polymer that has a constituent primary amine, and, as such, can form the amino-phosphate linkage to produce $R^2-(PO_2(PO_3)_n-OR^1)_s$ where, p=0, q=0, s≥1, and n=0 to 2.

Suitable polymers with constituent primary amine groups are polyvinylamines, polyacrylamides, and polyamino acids, preferably, polylysine. FIG. 1A shows a macromolecular prodrug of poly-L-lysine-araA.

In a second embodiment, $R^2$ can be a polymer that lacks constituent primary amine, and, as such, is derivitized to contain the primary amine by the addition of a linking group $(XNH)_q$, thereby forming $R^2-(XNH)_q(PO_2(PO_3)_n-OR^1)_s$ where, p=0, q≥s≥1, and n=0 to 2.

$R^2-(XNH)_q$ can be formed from polysaccharides, polyvinylic polymers, and combinations thereof, that possess reactive groups other than hydroxyls or primary amines. These polymers are derivatized to contain the primary amine via reaction with an XNH linking group. Example polymers include polyglutamate and polyaspartate as seen in Examples 22 and 35.

Figure 1B:
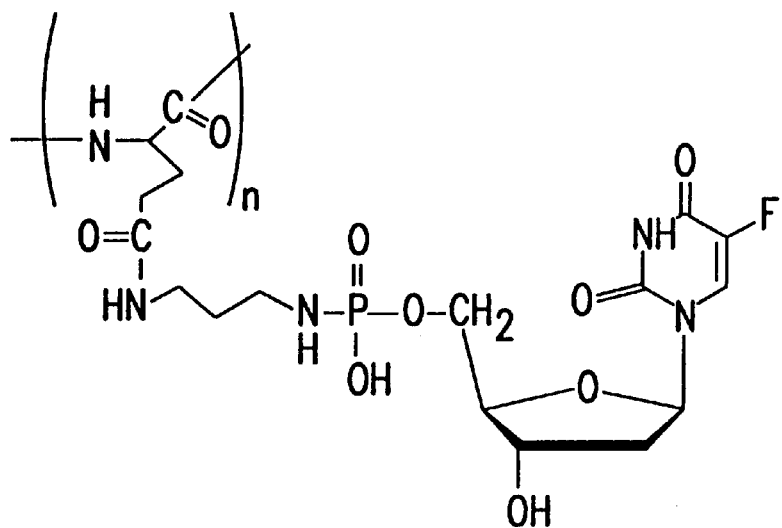
FIG. 1B shows the macromolecular carrier, polyglutamate coupled to the linking group ethylene diamine (EDA), and cojugated to FUDR monophosphate (P-FUDR).

XNH linking groups include lysine, polylysine, ornithine, polyornithine, or preferably a diamine. Suitable diamines include:

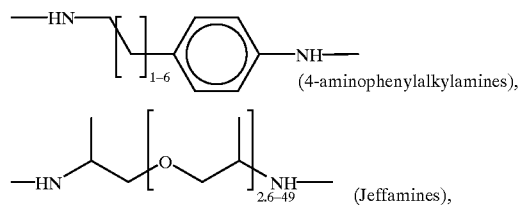
(4-aminophenylalkylamines), (Jeffamines), more preferably, $-HN(CH_2)_{0-6}NH-$. FIG. 1B shows the macromolecular prodrug Polyglutamic acid-FUDR with ethylene diamine as the linking group.

In another embodiment, $R^2$ can be a polymer that lacks constituent primary amines and other reactive groups except for hydroxyl groups. As such, the carrier is a polymeric composition modified at the hydroxyl groups with a bridging group $(Y_p)$, which is further derivitized to contain the primary amine via the linking group $(XNH)_q$, thereby forming $R^2-(Y)_p-(XNH)_q-(PO_2(PO_3)_n-OR^1)_s$ where, p≥q≥s≥1, and n=0 to 2.

$R^2$ can be polysaccharides, polyvinylic polymers, and other non-protein biocompatible polymers, and combinations thereof, that contain at least one terminal hydroxyl group, such as polyvinylpyrollidone, poly(oxyethylene) glycol (PEG), maleic anhydride divinylether (DIVMA), cellulose, and more preferably, pullulans, inulin, polyvinyl alcohol (PVA), N-(2-hydroxypropyl)methacrylamide (HPMA), and most preferably dextran and hydroxyethyl starch (HES).

Figure 1C:
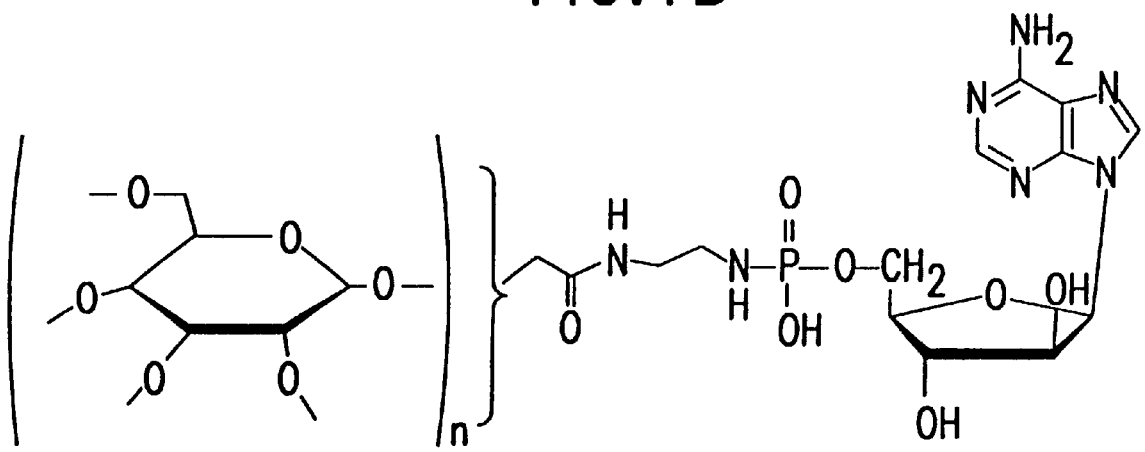
FIG. 1C shows the macromolecular carrier, dextran coupled to a carboxymethyl bridging group (CM) and an ethylene diamine linking group (EDA) coupled to the nucleotide analog araA monophosphate (P-araA).

The nature of the bridging group $-(Y)_p$ may vary. The bridging group may be formed from oxygen containing groups such as straight chain acyl groups of $C_{2-10}$, (including ketones, aldehydes, esters, acids, ethers), substituted amides (e.g., imidocarbonate), alcohols or combinations thereof. Best results are obtained when the bridging group is a carboxymethyl group ($-CH_2CO-$), or an isopropyl alcohol ($-CH_2(CHOH)(CH_2)-$) group. FIG. 1C shows the macromolecular prodrug Dextran-araA with carboxymethyl groups as the bridging group and ethylene diamine as the linking group.

$OR^1$ is a nucleoside analog. Nucleoside analogs in any stereochemical configuration (D vs L or α vs β) can be used. In a preferred embodiment, the phosphate group ($-PO_2-(PO_3)_n$) is attached at the position where the addition of further phosphate groups will produce the active antimetabolite. For example with araA, araC, ddI, AZT, and 5 FUDR the phosphate would be on the 5' position of the sugar. Acyclic nucleoside analogs like acyclovir or ganciclovir can be used provided that the phosphate that is attached to the primary amine of the carrier is added at a position metabolically analogous to the 5' position.

The number of phosphate groups per nucleoside analog, n, can be 0, 1 or 2, defining the phosphorylation state of the nucleoside analog as mono-, di- or triphosphate. The levels of modification, p, q and s, represent the numbers of molecules of bridging group (Y), linking group (XNH), and nucleoside analogs ($OR^1$) per mole of carrier. When p, and q are ≥1, the number of bridging groups $(Y_p)$, can be equal to or exceed the number of linking groups $(XNH_q)$ which can be equal to or exceed the number of nucleosides ($OR^1$) attached. The invention assumes that there is at least one mole of nucleoside analog per carrier (s≥1), and can have up to 100 or more.

In the Examples, the level of modification obtained is expressed as mmoles/g, where a gram is a gram of dry, final product. Expressed in this manner, the level of modification is independent from the purity of the sample; no correction is made for water content, or the presence of other low molecular weight impurities. Table 1 provides estimates for the ranges p, q and s per mole, referred to as the extent of derivatization, for some of the materials shown in examples. To estimate the extent of derivatization, a purity and molecular weight must be known. The materials are assumed to be 100% pure and have a molecular weight 1.25 times that of the carrier. The following formula provides a calculation to estimate the extent of derivatization:

$$\frac{\text{Term.Group.}}{\text{mole}} = \frac{m \text{ moles nucleoside analogue groups/g } (10^3)}{1 \text{ g/(MW Conjugate)}}$$

where 'Term group' refers to the any of the terminal groups attached to $R^2$ during the synthesis of the final prodrug, i.e., p, q or s.

It can be seen in Table 1 that the levels of derivatization vary widely, ranging from 8.5 FUDr molecules per mole of conjugate (Example 24), to 72 araA molecules per mole of conjugate (Example 38). Similarly, levels of derivatization vary widely with amino or carboxylated derivatives of the carrier.

TABLE 1

Estimates of Extent of Derivatization

| Example No. | Carrier, Term. Group | mmole/ g | Molecular Weight of Carrier | Term. Group/ mole |
|---|---|---|---|---|
| 1 | Dex T-10, CM | 1.3 | 10 | 16.3 |
| 2 | HES (75), CM | 1 | 75 | 94 |
| 3 | Dex T-10, CM | 1.3 | 10 | 16.3 |
| 4 | Dex T-40, CM | 1.3 | 40 | 65 |
| 5 | Dex T-70, CM | 1.3 | 70 | 118 |
| 6 | PVA(16), CM | 0.58 | 16 | 11.6 |
| 7 | HES(75)-CM, EDA | 1 | 75 | 94 |
| 18 | HES(75)-IPA, BDA | 0.45 | 75 | 42 |
| 23 | Dex(40)CM, EDA | 0.6 | 40 | 30 |
| 24 | Dex(40)-CM-EDA, FuDr | 0.17 | 40 | 8.5 |
| 25 | Dex(70)CM-EDA, araC | 0.179 | 70 | 15.7 |
| 28 | Dex(70)CM-EDA, Riba | 0.4 | 70 | 35 |
| 31 | Dex(70)CM-EDA, AZT | 0.399 | 70 | 35 |
| 35 | PolyG(25)EDA,araA | 0.81 | 25 | 25 |
| 36 | HES(75)IPA-EDA, araC | 0.54 | 75 | 51 |
| 38 | HES(75)CM-EDA, araA | 0.76 | 75 | 72 |
| 39 | Dex(T70)CM-EDA, ACV | 0.14 | 70 | 12.2 |

Abbreviations: Dex, Dextran, HES, hydroxyethyl starch; PolyG, polyglutamate; PVA, polyvinyl alcohol; molecular weight in parenthesis; IPA, isopropyl alcohol; CM, carboxymethyl; EDA, ethylene diamine; BDA, butane diamine.

Based on the above, when $R^2$ is dextran T40, Y is carboxymethyl (CM), XNH is ethylene diamine (EDA), $OR^1$ is FUDR, n=0, p=16.3, q=10, s=5, the prodrug in Example 24 can be estimated to have the following extent of derivatization:

Dextran (T40)-$CM_{65}$-$EDA_{30}$—$(PO_2$-FUDR$)_{8.5}$

Macromolecular prodrugs can be used to treat any viral infection of an animal or human, including but not limited to HIV, HCV, HBV, and herpes. Macromolecular prodrugs can be used to treat any cancer of an animal or human, including but not limited to carcinomas, sarcomas, lymphomas, and melanomas. These prodrugs can be prepared for administration by intravenous, subcutaneous, intramuscular or intradermal injections using the appropriate formulating agents available to the skilled artisan. With their high water solubility and molecular weight, the preferred routes of administration for macromolecular prodrugs are parenteral.

Activity of the Prodrugs

The macromolecular prodrugs of the invention can have a high solubility in water, and can be charged at physiological pH. The phosphoramide (—NH—$PO_2$—) bond used to link the carrier to the nucleotide analog produces prodrugs that are stable in plasma, stable over a wide range of temperatures and pH, are resistant to enzymatic degradation by phosphatases and other enzymes. After cell uptake, the prodrugs are cleaved in a manner that releases a therapeutically active form of the nucleoside analog. In complex systems cleavage can occur in a variety of ways that yield therapeutically active agents, with the preferred method of cleavage being between the (—NH—$PO_2$—) bond.

Stability in Plasma

Figure 5:
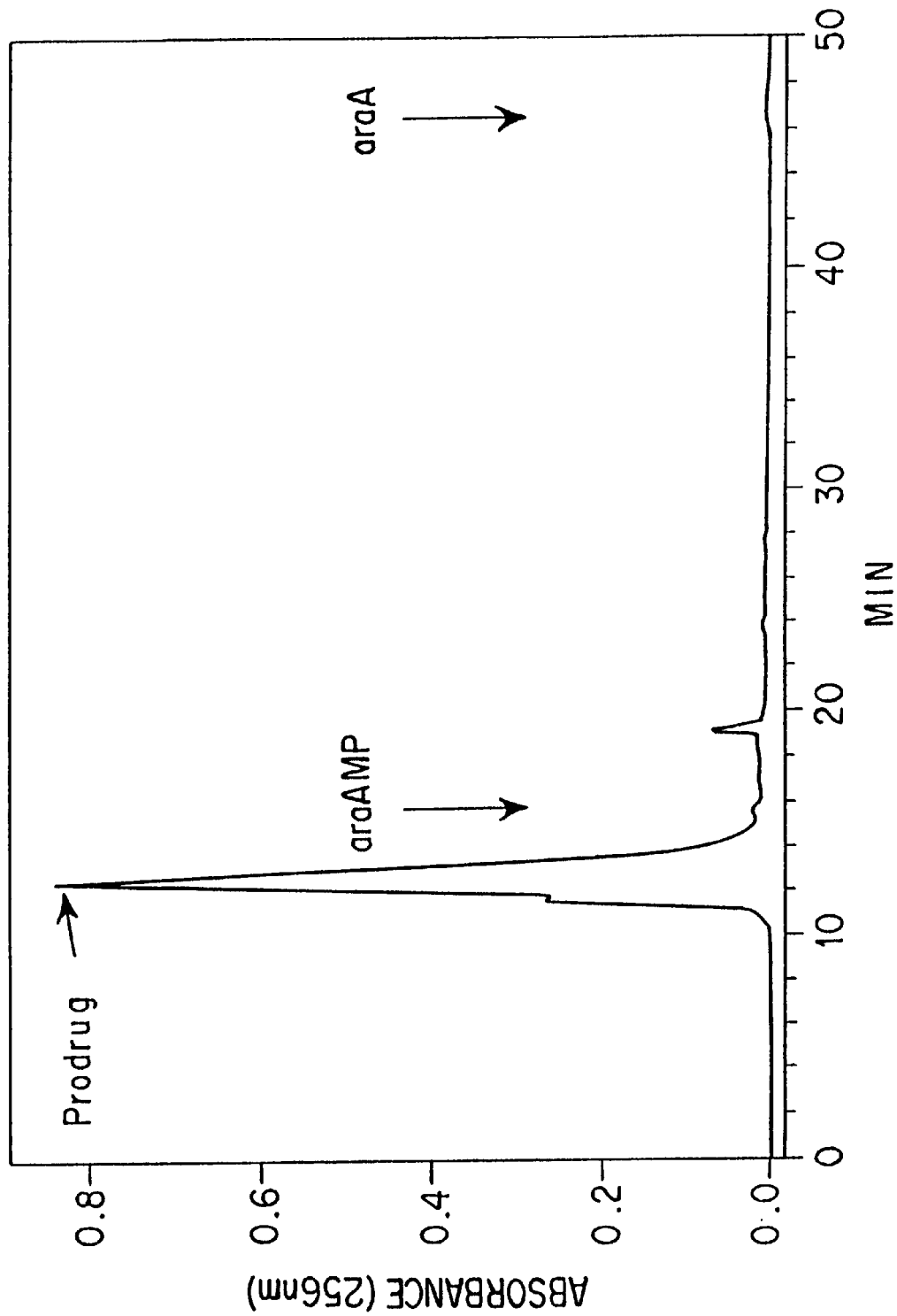
FIG. 5 is a GPC chromatogram of a carboxymethyl dextran-ethylene diamine-araAMP (Dextran (10 kDa)-CM-EDA-P-araA) prodrug made according to the teachings of Example 41, after incubation in plasma demonstrating the stability of the prodrug in human plasma. (GPC conditions: Waters UHG 250 Column (300×7.8 mm I.D.) 0.5 mL/min, 20 mM PO$_4$, pH 7, 0.1 NaCl).

A dextran-araA prodrug made according to the teachings in Example 41 was evaluated for stability in plasma and releasability as described in Example 43. After incubation in human plasma for 37° C. for 1 hr there was no indication of breakdown products, particularly araA or araA monophosphate (FIG. 5).

Lability with Cell Extracts

Figure 6:
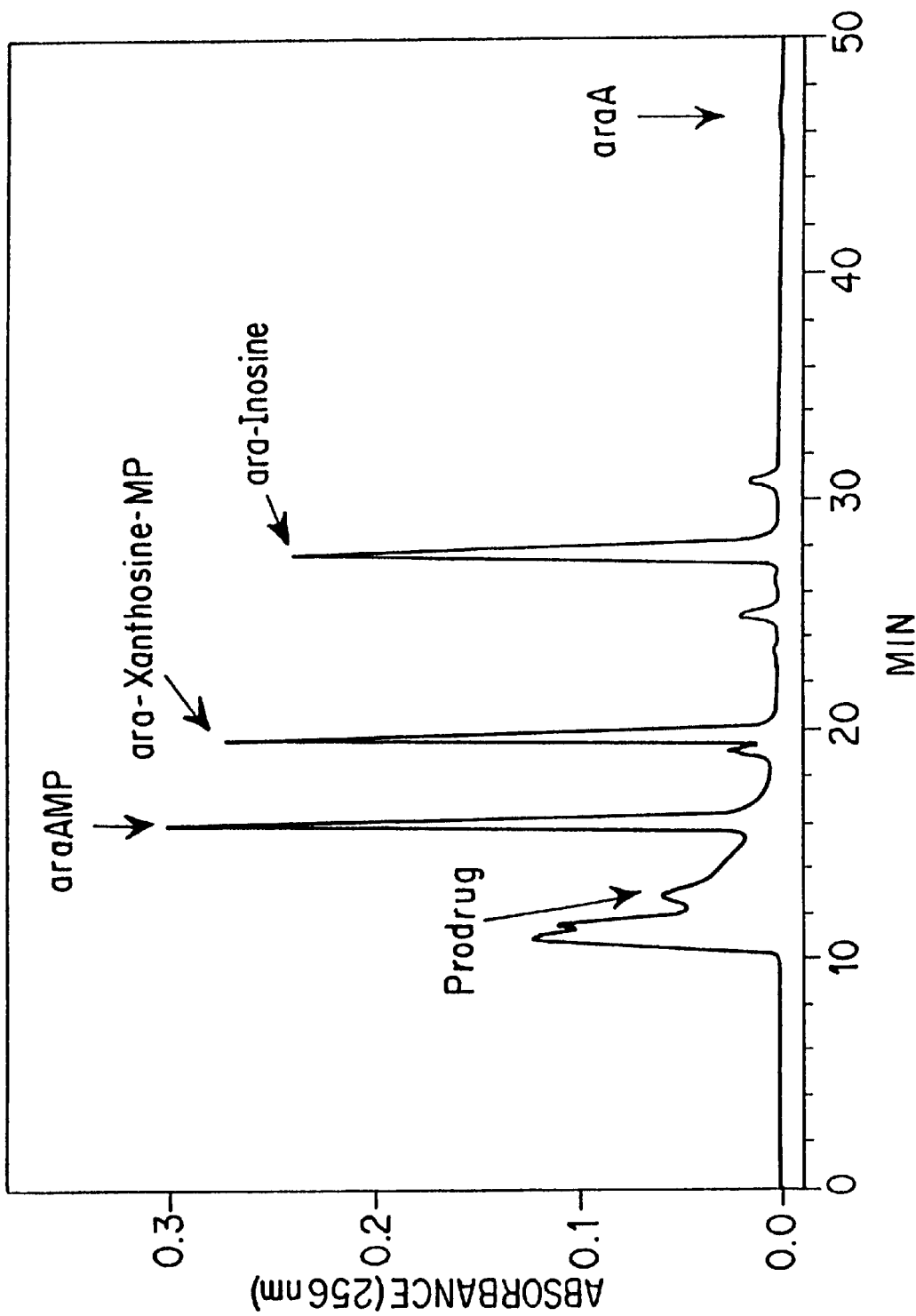
FIG. 6 is a GPC chromatogram of carboxymethyl dextran-ethylene diamine-araAMP (Dextran (10 kDa)-CM-EDA-P-araA) prodrug made according to the teachings of Example 41 and standards after incubation in liver extract demonstrating release of the nucleotide analog from the prodrug in tissue extracts. (GPC conditions: Waters UHG 250 Column (300×7.8 mm I.D.) 0.5 mL/min, 20 mM PO$_4$, pH 7, 0.1 NaCl).

A dextran-araA prodrug made according to the teachings in Example 41 was evaluated for lability (releasability) in liver extracts as described in Example 43. The chromatogram in FIG. 6 shows that the prodrug breaks down readily in liver extract, as evidenced by the peaks for araA, araxanthosine monophosphate and araInosine.

The data from the release assay and the stability assay demonstrate surprisingly that the prodrugs of the invention have both excellent stability in extracellular fluids (plasma), yet breakdown readily in tissue extracts.

Antiviral Activity

A common method of evaluating the success of antiviral and anticancer agents is by measuring the efficacy and toxicity in tissue culture systems. The antiviral activity of the macromolecular prodrug made according to the teachings in Example 40 was evaluated in Hep G2 cells, a common assay for evaluating efficacy and toxicity of agent for Hepatitis B, as described in detail in Example 42.

The prodrug of the invention demonstrated its capability in traversing cell membranes and, once inside the cells, showed significantly increased antiviral activity with a corresponding decrease in toxicity over the unconjugated nucleoside araA. This is evidenced by the prodrug's 20-fold improvement in the efficacy value (the $EC_{90}$ values of Table 3), coupled with the corresponding 15-fold decrease in toxicity (the $CC_{50}$ values of Table 3) when compared with the parent nucleoside araA. It was deduced that the increase in antiviral activity of the prodrug was the result of a more beneficial metabolism of the prodrug. Indeed, if improved delivery alone occurred both the values for toxicity and efficacy for the prodrug would be increased by the same ratio over the unconjugated araA, and the ratio of toxicity to efficacy (the SI value of table 3) would be the same for both araA and the prodrug of araA. It is further seen that when araA is used to synthesize macromolecular prodrugs it is transformed from a compound with an SI less than β-L-FTC (SI for araA: 11; β-L-FTC: 678) to one with an SI greater than β-L-FTC (Conjugate: 4200). This infers that macromolecular prodrugs of nucleotide analogs can improve the safety and efficacy of nucleotide analogs made from nucleoside analogs by overcoming poor transport into or poor phosphorylation inside cells.

Other appropriate methods can be used to test for the antiviral activity of other prodrugs of the invention against other viruses. For example, to assess the antiviral potential of the conjugate against Hepatitis C, surrogate test cultures, such as yellow fever virus (Vero kidney cells) and Bovine diarrhea virus in bovine kidney cells are used, as no culture for Hepatitis C currently exists.

The prodrugs can be assessed for anticancer activity by the methods known in the art for determining anticancer activity, for example, in murine tumor models such as murine leukemias (L1210 and P388 cell line), B16 melanomas, M5076 fibrosarcoma, and other breast and colon carcinomas.

Synthesis of Macromolecular Prodrugs

Table 3 summarizes several of the combinations of macromolecular polymers, bridging groups, linkers and nucleotide analogs that can be employed in practicing the invention. Any of the polymers in the left column can be derivatized with any of the bridging groups in column 2. Furthermore, as described above, the derivatized carrier can be further coupled to any of the linking groups in column 3 followed by conjugation to any nucleotide analogs in column 4. Alternatively, the diamines from column 3 can be reacted with the nucleotides from column 4 and subsequently coupled to the derivatized carriers from columns 1 and 2.

In Scheme 1 (FIG. 2) a macromolecular polymer (MP—OH) is first reacted with a halogenated acetic acid (bromoacetic acid as an example) under alkaline conditions to add a carboxymethyl bridging group (—CH$_2$COOH). In a separate reaction, the nucleoside analog (NsAn) is phosphorylated to a nucleotide analog (H$_2$PO$_2$NsAn) at the 5'OH position. (The O at the 5' position of the nucleoside analog is omitted from the schemes as it is assumed to part of the NsAn structure.) The resulting nucleotide analog is then reacted with the diamine linking group in the presence of carbodiimide (CDI). The derivatized macromolecular polymer (polymer and bridging group) is reacted with the amine linking group-nucleotide intermediate, again in the presence of CDI, to form the prodrug.

In Scheme 2, the macromolecular polymer-bridging group is reacted with the amine linking group to form the carrier (polymer-bridging group-amine terminated linking group). The carrier is reacted with the nucleotide to form the prodrug conjugate. It should be appreciated that reaction pathways in Schemes 1 and 2 result in the same prodrug.

In Schemes 3 and 4 (FIG. 3), the macromolecular polymer MP—OH is reacted with epichlorohydrin or epibromohydrin to add a different type of bridging group to the polymer, an isopropyl alcohol group (—CH$_2$CHOHCH$_2$—). As in Schemes 1 and 2, the nucleoside is converted to a nucleotide,

TABLE 2

Example Components Of Macromolecular Prodrugs
Of Nucleoside Analogs ($p \geq q \geq s \geq 1$, $n = 0 - 2$)

| 1<br>Macromolecular<br>Carrier, R$^2$— | 2<br>Bridging Group<br>—Y$_p$— | 3<br>Linking Group<br>Diamine [—XNH—]$_q$ | 4<br>Nucleotide Analog<br>—(PO$_2$(PO$_3$)$_n$OR$^1$)$_s$ |
|---|---|---|---|
| Dextran (T10) | —CH$_2$—CO—<br>carboxymethyl | —HN—NH—<br>hydrazine | araA<br>FUDR |
|  | —(CH$_2$)$_6$—CO—<br>hexanoic acid | —HN—(CH$_2$)$_2$—NH—<br>ethylene diamine | dA<br>ddA |
| Dextran (T40) | —CH$_2$—CHOH—CH$_2$—<br>isopropyl alcohol | —HN—(CH$_2$)$_4$—NH—<br>butane diamine | ribavirin<br>araC |
| Dextran (T70) | imidocarbonate | —HN—(CH$_2$)$_6$—NH—<br>1,6-hexane diamine | FIAU<br>ddI |
| Cyclodextran<br>Hydroxyethyl<br>starch (HES) |  | —HN—[...]$_{1-6}$—⟨phenyl⟩—NH— | AZT<br>acyclovir |
| Polyvinyl alcohol (PVA)<br>HPMA<br>PVP |  | 4-aminophenylethylamine<br>lysine, polylysine |  |

Figure 2:
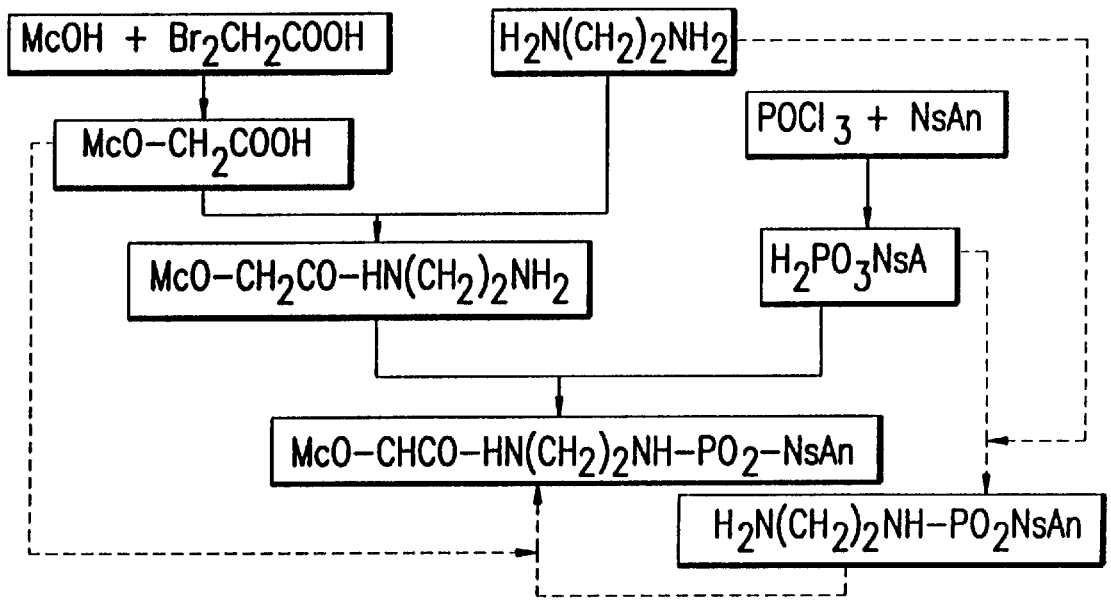
FIG. 2 demonstrates two generalized reaction pathways for making a prodrug of the invention when a linking group and a carboxymethyl type bridging group are used. A halogenated acetic acid is reacted with a macromolecular polymeric carrier (MP—OH) to form the carrier-bridging group formulation. The linking group can be reacted with the nucleotide analog, which is then reacted with the carrier formulation (Scheme 1). Alternatively, the macromolecular polymeric carrier-bridging group formulation can be reacted with the linking group, and subsequently with the nucleotide analog (Scheme 2) to form the prodrug.
Figure 3:
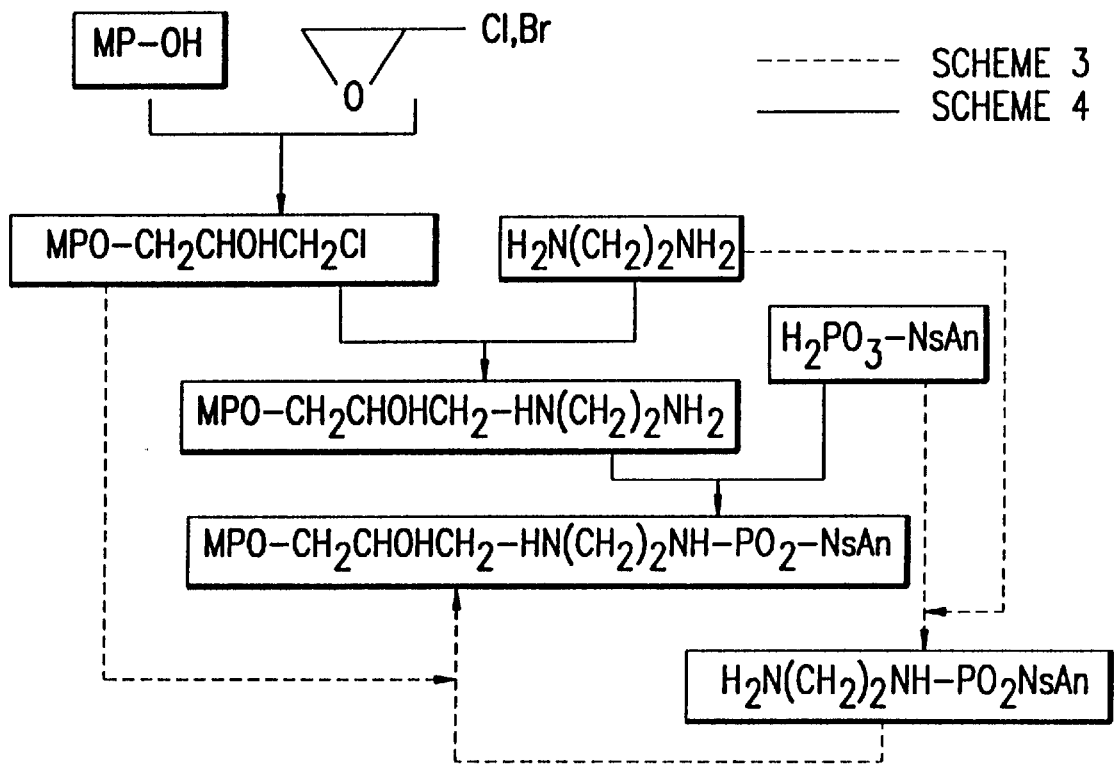
FIG. 3 demonstrates another generalized reaction pathway for making a prodrug of the invention. An epihalohydrin is reacted with a macromolecular polymeric carrier (MP—OH) to form the carrier-bridging group formulation with an isopropyl alcohol bridging group. The linking group can be reacted with the nucleotide analog, which is then reacted with the carrier formulation (Scheme 3). Alternatively, the macromolecular polymeric carrier-bridging group formulation can be reacted with the linking group, and subsequently with the nucleotide analog (Scheme 4) to form the prodrug.
Figure 4:
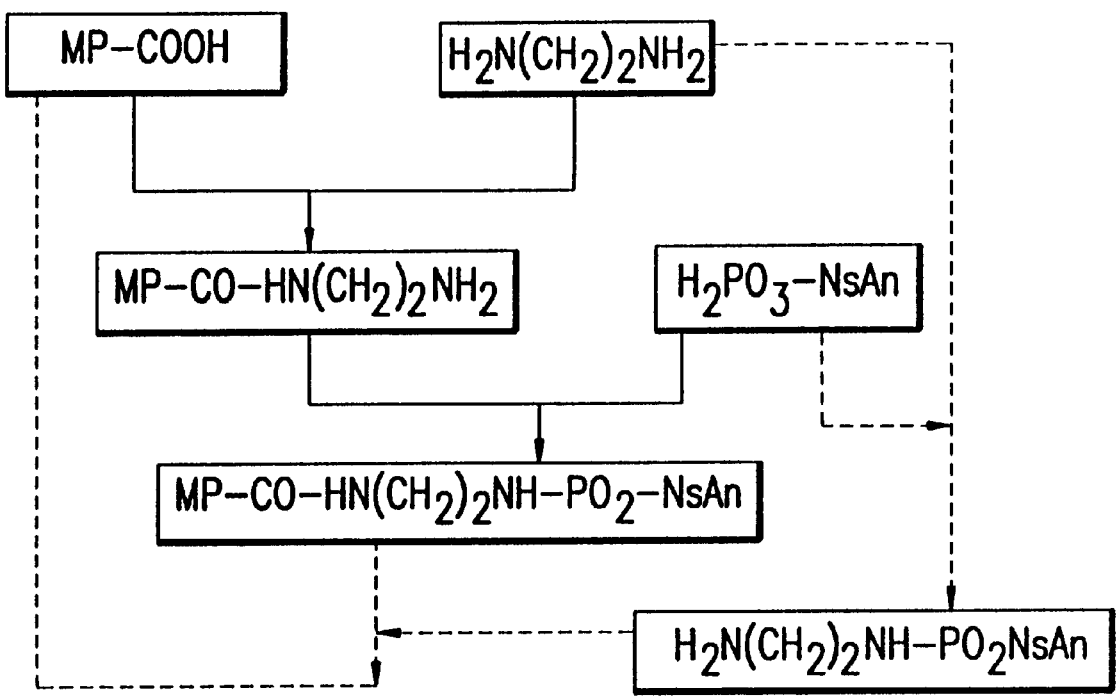
FIG. 4 demonstrates the generalized reaction pathways that can be used when no bridging group is used. In Scheme 5, the linking group is reacted with the nucleotide analog, and this composition is subsequently reacted with the carrier to form the prodrug. Alternatively, the linking group is reacted directly with the carrier, and this formulation is subsequently coupled to the nucleotide analog (Scheme 6).

Several general strategies for synthesizing the prodrugs are provided in the accompanying examples, and generalized reaction pathways are shown in FIGS. 2, 3, and 4. FIGS. 2 and 3 describe the possible pathways that can be used when the R$^2$ composition includes a linking group and a bridging group (p,q$\geq$1). FIG. 4 shows the possible pathways when the R$^2$ composition includes a linking group (p=0, q$\geq$1). In the six schemes, a monophosphate nucleotide analog is shown in the pathways (n=0, s$\geq$1); however, the di- and tri-phosphates forms can be substituted in the reactions.

Ethylene diamine is shown as an example linking group in Schemes 1–6. Reagents such as base, carbodiimide and other reaction by-products are not shown in the pathways. The nucleotide analogs may be obtained commercially or synthesized from the corresponding nucleoside analogs.

then reacted with the an amine linking group to form the amine linking group-nucleotide analog intermediate (Scheme 3). The polymer-bridging group and amine linking group are reacted to form the prodrug conjugate.

In Scheme 4, the polymer-bridging group product is reacted with the amine linking group to form the complete carrier (polymer-bridging group-amine linking group), which is then reacted with the nucleotide to form the prodrug conjugate.

In Schemes 5 and 6 (FIG. 4) the macromolecular polymer chosen (MP—COOH) has groups of sufficient reactivity such that no bridging group is necessary p=0) between the polymer and the amine linking group-nucleotide intermediate. To form this prodrug, the amine linking group can be attached to the the nucleotide analog and this combination subsequently can be reacted with the macromolecular polymer (Scheme 5). Alternatively, the macromolecular polymer can be reacted with the bridging group, and this formulation subsequently reacted with the nucleotide analog (Scheme 6).

The preference of using one reaction scheme over another is generally made on the basis of such criteria as purity of the final product, ease of isolation, yield, etc.; however, some general considerations regarding the synthesis of the macromolecular prodrugs follow.

When bifunctional reagents are used to form the macromolecular carriers (e.g., epichlorohydrin, epibromohydrin), reaction conditions must be adjusted to minimize cross-linking between macromolecular polymer chains. In general decreasing the concentrations of carrier may lead to unacceptably low degrees of modification, or require the use of unacceptably large reaction vessels, whereas increasing the concentrations of carrier tend to promote crosslinking. Cross-linking is evident by an increase in molecular weight, which can be monitored by any of the usual techniques for measuring molecular weight; size exclusion chromatography or by light scattering are satisfactory. Cross-linking may be minimized by adjusting the concentration of macromolecular carrier in the reaction, and by:

(i) using high molar ratios of bifunctional reagents to macromolecular polymer during formation of the carrier;

(ii) varying the order of the conjugation reaction, i.e. attaching the amine linking group to the carrier, then coupling the nucleotide analog to the carrier complex (FIG. 2, Scheme 1), rather than coupling the macromolecular carrier to the amine linking group derivative of the nucleotide analog (FIG. 2, scheme 2);

(iii) using as a linking group a molecule with 2 primary amino groups with differing reactivities either within the same molecule (4-aminophenylalkylamine) or between different molecules (ethylene diamine vs butane diamine);

(iv) using amino acids with blocked carboxyl groups, to react the amino groups with the nucleotide, then deblocking the carboxyl group.

Thus, the conditions for modifying the macromolecular carrier need to be selected empirically for a given macromolecular carrier and modification chemistry.

Unreacted, low molecular weight materials can be removed from high molecular macromolecular carrier based compounds using ultrafiltration, gel filtration chromatography or other techniques.

The phosphorylation reaction to convert nucleoside analogs to the corresponding nucleotide analogs can have different degrees of efficiency. Purification procedures, such as chromatography and precipitation, can be used to yield pure nucleotide analog.

When diamines are reacted with nucleotide analogs, crosslinking can yield dimers, which can be represented as NsAn—$PO_2$—NH—X—NH—$PO_2$—NsAn. These dimers lack a primary amine and, in this form, cannot react with the macromolecular carrier. The presence of such structures can be ascertained by ion exchange HPLC or by capillary zone electrophoresis. Techniques for limiting the formation of these dimers include adjusting the concentrations of reactants and the molar ratios the diamine to nucleotide analogs.

The degree of modification of the macromolecular carrier is measured by appropriate analytical methods. When the macromolecular carrier is modified by reaction with epichlorohydrin or epibromohydrin, the extent of chlorination or bromination can be measured by elemental analysis. The content of amino or carboxyl groups can be measured by titration with acid or base, or by analytical methods where these groups are subjected to chemical modification, e.g. reaction with ninhydrin for amino groups.

The number of nucleoside analogs per gram of prodrug can be determined from UV absorbance utilizing the extinction coefficient of the base of the nucleoside analog. Alternatively, radioactive nucleoside analogs can be used during synthesis and the specific activity of the prodrug used to verify the loading based on UV absorbance.

The existence of an —NH—$PO_2$— linkage can be determined by measuring the release of the nucleoside analogs in acid. Relatively mild acids like perchloric acid 12%, 15 minutes, 37° C. readily cleave phosphoramide linkages while other types of linkages (peptide, ether, and phosphoester) are more stable. Linkage can also be ascertained from $^{13}$C or $^2$H NMR spectra.

There are a number of routes to synthesize the macromolecular prodrugs described in this invention, and, although several general strategies are described, pathways other than those described in the specification and figures are conceivable; the invention should not be considered to be limited only to these embodiments.

EXAMPLES

Example 1

Dextran (T10)-CM (Carboxymethyl Dextran)

Aqueous solutions were prepared of Dextran T10 (250 mg/ml, Pharmacia), 8M sodium hydroxide, 2.1 M bromoacetic acid, and 6M HCl. The Dextran T10 and HCl solutions were used at temperatures in the range of 22–25° C., and the NaOH and bromoacetic acid solutions were refrigerated to 4–8° C. before carrying out the reaction.

Dextran T10 (20 mL of the solution) in water at 22–25° C. was placed in a beaker. While stirring the solution, 24 mL of 8 M NaOH at 4–8° C. was added quickly (about 10 seconds). After 5 minutes 13 mL of 2.1 M bromoacetic acid (3.85 g dissolved in 13 mL of water) at 4–8° C. was added to the stirring solution. The flask was rinsed with 5 mL of water and the rinse water was added to the reactants. The reaction solution was maintained at 22–25° C. After 120 minutes the reaction was terminated by neutralization with 6 M HCl. The solution was diluted to a volume of 200 mL with distilled water (DIW) and ultrafiltered against a 3000 MWCO (molecular weight cut off) membrane to a volume of 20 mL, reconstituted to a volume of 200 mL with DIW and the ultrafiltration cycle repeated for a total of 5 ultrafiltration cycles. After the last ultrafiltration cycle the retained solution was frozen and lyophilized. The recovered solid was carboxymethyl Dextran T10 (sodium salt), with a carboxyl content of approximately 1.3 mmoles carboxyl per gram product.

Example 2

Carboxymethyl Hydroxyethyl Starch (HES)(HES-CM)

Aqueous solutions were prepared of hydroxyethyl starch, (250 mg/mL, Ajinomoto Corp), 8M sodium hydroxide, 2.1 M bromoacetic acid, and 6M HCl. The HES and HCl solutions were used at temperatures in the range of 22–25° C., and the NaOH and bromoacetic acid solutions were refrigerated to 4–8° C. before carrying out the reaction.

Hydroxyethyl starch (20 mL of the solution) at 22–25° C. was placed in a beaker. While stirring the solution, 24 mL of 8 M NaOH at 4–8° C. was added quickly (about 10 seconds). After 5 minutes 13 mL of 2.1 M bromoacetic acid (3.85 g dissolved in 13 mL of water) at 4–8 ° C. was added to the stirring solution. The flask was rinsed with 5 mL of water and the rinse water was added to the reactants. The reaction solution was maintained at 22–25° C. After 120 minutes the reaction was terminated by neutralization with 6 M HCl. The solution was diluted to a volume of 200 mL with distilled water (DIW) and ultrafiltered against a 3000 molecular weight cut off (MWCO) membrane to a volume of 20 mL, reconstituted to a volume of 200 mL with DIW and the ultrafiltration cycle repeated for a total of 5 ultrafiltration cycles. After the last ultrafiltration cycle the retained solution was frozen and lyophilized. The recovered solid was carboxymethyl HES (sodium salt), with a carboxyl content of approximately 1.0 mmoles carboxyl per gram product.

Example 3

Carboxymethyl Dextran (T10)

Dextran (T10)-CM was prepared following the procedure in Example 1, substituting 13 mL of chloroacetic acid (2.1 M) for bromoacetic acid. The recovered product was carboxymethyl Dextran (sodium salt), with a carboxyl content of approximately 1.3 mmoles carboxyl per gram product.

Example 4

Carboxymethyl Dextran (T40) (Dextran (T40)-CM)

Dextran T-40 (CM) was prepared following the procedure in Example 1, substituting Dextran (T40) for Dextran (T10). The recovered product was carboxymethyl Dextran (T40) sodium salt with a carboxyl content of approximately 1.3 mmoles carboxyl per gram of product.

Example 5

Carboxymethyl Dextran (T70) (Dextran (T70)-CM)

Dextran T-70 (CM) was prepared following the procedure in Example 1, substituting Dextran (T70) for Dextran (T10). The recovered product was carboxymethyl Dextran (T70) sodium salt with a carboxyl content of approximately 1.3 mmoles carboxyl per gram of product.

Example 6

Carboxymethyl Polyvinyl Alcohol (PVA-CM)

Polyvinyl alcohol (PVA, 5 g, Scientific Polymer Products) was suspended in 50 ml water. It was stirred with a magnetic stirrer and warmed at 70° C. for 15 min to dissolve, then cooled to 25° C. Cold (4° C.) 8 M NaOH (35 ml) was added to the PVA solution, and stirred at 25° C. for 5 min. Fine particles precipitated from the reaction mixture. Solid bromoacetic acid (5.91 g) was added. The reaction mixture was stirred and the temperature was maintained between 20–25° C. After 2 h the reaction mixture was diluted with ice to 200 ml and neutralized with 6 M HCl (ice cold). The neutral reaction mixture was warmed to 70° C. until the fine particles dissolved, then cooled to 25° C. and filtered through a 0.45 m filter. The solution was ultrafiltered against DI water (1.7 L), using an Amicon stir cell with a 3000 molecular weight cutoff membrane. The solution was concentrated to 150 ml and lyophilized. Yield was 6.03 g, which is more than 100% because of the water content of the product.

The carboxymethyl content was determined by titration. The carboxymethyl content was 0.5836 mmol/g, obtained as the average of three measurements.

Example 7

Hydroxyethyl Starch-IPA-EDA

A 1 L flask was charged with 21.5 g NaOH and 500 ml de-ionized water. The solution was cooled to 10° C., and 10 g HES (Heta-starch, Ajinomoto Co., Tokyo, Japan). When the carbohydrate was dissolved, 50 ml of epichlorohydrin was added. The cooling bath was removed, and the heterogeneous mixture was vigorously stirred for 24 h. The mixture was cooled to 5° C., and 200 ml ethylene diamine (previously cooled to 10° C.) was added. The solution was heated to 65° C. over 30 min., the heat source was removed, and the solution was stirred for 24 h. After 24 h, 6 M HCl was added until the pH of the solution was pH 9.0, cooling as necessary to keep the temperature below 30° C. The solution was diluted to 2.5 L with de-ionized water, and ultrafiltered against a YM-3 filter (Amicon, MWCO 3000) in a 2.5 L stir cell ultrafiltration apparatus (Amicon). After the fifth concentration, the retentate was filtered through a 0.2 $\mu$m filter, and lyophilized. Yield: 12.95 g. A ninhydrin-based end group analysis indicated there was 1.0 mmol EDA/g HES-IPA-EDA.

Example 8

Lysine-P-AraA

Either the methyl ester or ethyl ester of 1-lysine is coupled to araAMP using water soluble carbodiimide(1-(3-dimethylaminopropyl)-3-ethylcarbodiimide or EDAC) as the coupling agent and (optional) hydroxybenzotriazole (HOBT) as a catalyst. The araAMP and lysine ester are coupled through a phosphoramide (N—P) bond between the 5' phosphate of araAMP and either the $\alpha$ or $\epsilon$ amine of the lysine ester. The $\epsilon$ N—P bond is expected to be the predominant form due to steric effects.

Example 9

Ethylene Diamine-FUDR monophosphate (EDA-P-FUDR)

A. Preparation of P-FUDR

FUDR (6.645 g, 27 mmol, FUDR, PCR Incorporated, Gainesille, Fla.) was dissolved in trimethyl phosphate (70 ml ) and cooled to 2° C. DI water (48 ul, 2.7 mmol), pyridine (2.02 ml, 30 mmol), and phosphorous oxychloride (2.78 ml, 30 mmol) were mixed with 30 ml of trimethyl phosphate at 2° C. and stirred for 2 min. This solution was added to the FUDR solution dropwise over 30 min, then stirred at 2° C. for 30 min. These solutions were prepared and reacted together under inert atmosphere. Ice water (60 ml) was added and stirred at 2° C. for 1.5 h. The reaction mixture was mixed with 30 g of ice water and extracted with methylene chloride (100 ml×4) to remove trimethyl phosphate. The water phase was adjusted to pH 7 with 2M of LiOH at 3–5° C. over a 30 min period, concentrated to near dryness at 30° C. under reduced pressure, resuspended in 50 ml of water, and cooled to 3–5° C. in an ice-water bath. A precipitate consisting of lithium triphosphate was removed by filtration. The filtrate was concentrated to near dryness, redissolved in 40 ml of 50° C. DI water, and mixed with 100 ml of ethanol (70° C.). The solution was cooled to room temperature to precipitate the product. The precipitate was collected by filtration and washed with ethanol to give FUDR-5'-phosphate. Purity: 86% by HPLC.

The product was further purified to remove FUDR-3',5'-diphosphate by dissolving it in about 100 ml of water. Ethanol was added to the solution dropwise until the solution became cloudy. The cloudy solution was immediately centrifuged (at 5° C.) for 10 min and the precipitate was removed. The supernatant was mixed with 100 ml of ethanol and the precipitate was collected by filtration and washed with ethanol to give FUDR-5'-phosphate.

A sample was further purified with anion exchange chromatography by use of Dowex 1x2-400 resin. Sample (0.48 g) was dissolved in 5 ml of DI water and loaded the column ($HCOO^-$ form, column size 18 cm×1.5 cm). The column was eluted with 1M of formic acid isocratically. Fractions were collected with 100 drops each tube. The fractions were analyzed with HPLC. Fractions 81 to 190 (about 6 ml each) were combined and concentrated to about 2 ml and adjusted to pH 9.5 with 1M LiOH. The content was added to about 10 ml of 70° C. ethanol and the precipitated was collected by filtration and washed with ethanol to give 52 mg FUDR-5'-MP.

NMR (δ, ppm, in $D_2O$): $^1H$: 2.08–2.12(m, 2H), 3.60(t, 2H), 370–3.72(m, 1H), 3.89–4.34(m, 1H), 6.09–6.12(m, 1H), 7.71–7.73(d, 1H). $^{13}C$: 38.5(1C), 63.4(0.5C), 63.5 (0.5C), 71.0 (1C), 85.3(1C), 85.5(0.5C), 85.7(0.5C), 123.9 (0.5C), 124.3(0.5C), 140.6(0.5C), 143.3(0.5C), 156.8(1C), 167.5(0.5C), 167.7(0.5C). $^{31}P$: 4.67.

B. Preparation of EDA-P-FUDR 0.6 mL of ethylene diamine (0.538 g,) was dissolved in 2 ml of DI water and 0.35 ml of HCl (12M) was added dropwise. One gram of FUDR-5'-phosphate (3.69 mmol, 91% pure) was added and stirred until completely dissolved. The solution was adjusted to pH 6.3 with 6M HCl and heated to 50° C. with stirring. EDAC(1 g) was added and the reaction was stirred at 50° C. for 1 h. An additional one gram of EDAC was added and stirred at 50° C. for 30 min. The reaction mixture was adjusted to pH 10 with 1M LiOH and concentrated to a syrup.

The syrup was mixed with 40–50 ml hot ethanol (50° C.) and a precipitate was obtained. The precipitate was filtered and washed with ethanol. The product (0.54 g) was 87% pure by HPLC. The mother solution was concentrated and suspended in 20–30 ml of ethanol. The second precipitate was filtered and washed with ethanol to give 0.2 g of product, 89% pure). The sample was purified for NMR by ion-exchange chromatography.

Proton NMR of EDA-FUDR-5'MP
$^1H$ NMR($D_2O$): 2.21–2.27(m, 2H), 2.91–2.98(m, 4H, N—$CH_2$—$CH_2$—N), 3.85–3.89(m, 2H), 4.021–4.026(b, 1H), 4.38–4.40(m, 1H), 6.15(t, 1H), 7.95(d, 1H). $^{13}CNMR$: 38.2(1C), 38.7(1C), 40.67(1C), 63.7(1C), 70.5 (1C), 85.5 (2C), 123.9(0.5C), 124.3(0.5C), 140.6(0.5C), 143.3(0.5C), 156.8(1C), 167.5(167.7(0.5C).

Example 10

Ethylene Diamine AraC monophosphate
(EDA-P-araC)

AraCMP (266 mg, 0.82 mmol, Aldrich) and 70 ul (1.04 mmol) ethylene diamine were dissolved in 2.06 ml deionized water, and the pH was adjusted to 6.3 using 6M HCl at 50° C. The reaction was initiated by adding 312 mg (2×0.82 mmol) EDAC. The reaction was kept stirring at 50° C. for 2 hours before an additional 82 mg EDAC was added. The reaction was kept stirring at 50° C. for another hour, and HPLC showed that the reaction was completed. Ethanol (10 ml) was added to the reaction mixture, and the product was precipitated after standing 1 h at 4° C. The product was collected by filtration and redissolved in 1.5 ml water. Ethanol (4 ml) was added, the product was collected by centrifugation, and dried under vacuum. Yield: 250 mg.

Example 11

Ethylene Diamine-Acyclovir monophosphate
(EDA-P-ACV)

Preparation of P-ACV

Acyclovir (6.075 g, 27 mmol), trimethyl phosphate (65 ml, 0.56 mol), and DI water (48.2 ul, 2.7 mmol) were mixed under inert atmosphere and stirred at room temperature for 1 h with occasional sonication (5 min periods) to achieve a finely dispersed solid. The mixture was cooled with an ice bath (2° C.) for 10 min then $POCl_3$ (3 ml, 32 mmol) was added dropwise over 5 min. The ice bath was removed and the solution stirred at room temperature for 30 min.

The solution was cooled to 2° C. in an ice bath. Ice water (60 ml) of was added, and the reaction mixture stirred at 2° C. for 1 h. The solution was extracted with $CH_2Cl_2$ (50 ml×4). The water phase was adjusted to pH 8.5 using 2M LiOH with ice bath cooling, and stirred at 5–10° C. for 2 h. The pH was adjusted to pH 9 with 2M LiOH. The solution was concentrated to about 150 ml and then mixed with 250 ml of ethanol. The precipitate was collected by filtration and washed with ethanol, giving a solid.

The solid was dissolved in 250 ml of distilled water (60–70° C.). The mixture was cooled to room temperature and centrifuged at 10000 RPM for 30 min at 5° C. The supernatant was concentrated to about 50 ml and mixed with 80 ml of DMF. The resulting precipitate was sonicated for 5 min, collected by filtration and washed with DMF. The product was mixed with 60 ml of DMF and stirred at room temperature overnight. The precipitate was filtered, washed with DMF and ethanol, and dried under vacuum to give 8.3 g. Reverse phase HPLC showed 97% pure (C18 column, flow rate: 1 ml/min; fluent: 3% MeOH in 5 mmol $KH_2PO_4$, pH 3.6)

NMR (ppm) $^1H$: 3.48–3.50(m, 2H), 3.55–3.57(m, 2H), 5.24(s, 2H), 7.66(s, 1H). $^{13}C$: 62.7(d, 1C), 68.8(d, 1C), 72.5(s, 1C), 115.6(s, 1C), 139.8, (s, 1C), 151.3(s, 1C), 153.8(s, 1C), 158.7(s, 1C). $^{31}P$: 4.6(s, 1P).

Preparation of EDA-P-ACV 0.6 ml of ethylene diamine was dissolved in 1 ml of DI water and HCl (12M, 1.8 ml) was added dropwise to adjust the pH to 6.5–6.6 at room temperature. One gram of Acyclovir-phosphate (3.15 mmol) was added and stirred at 54° C. Water (2.4 ml) was gradually added and pH dropped from 6.6 to 5.97. The solid was not completely dissolved. EDAC-HCl(2 g) was added portion-wise over about 1 min and stirred at 56° C. for 20min (pH 6.2).

An additional 0.6 g of EDAC was added and the reaction was stirred at 50° C. for 50 min. The reaction was cooled with ice, and a precipitate formed which was filtered and washed with 2° C. water(1 ml), $H_2O$/ethanol (1:1, 4 ml), and ethanol (10 ml) to give white solid product 0.65 g. The product was resuspended in water (about 2 ml) and mixed with 15 ml of ethanol to give purified EDA-P-ACV. $^1HNMR$ (ppm): 2.88(br s, 4H), 3.62(s, 2H), 3.76(s, 2H), 5.38(s, 2H), 7.80(s, 1H).

Example 12

Ethylene Diamine-FIAU monophosphate
(EDA-P-FIAU)

A. Preparation of FIAU-5'-monophosphate

FIAU was synthesized according to the literature procedure [H. G. Howell, et al: J. Org. Chem, Vol 53, 88–92 (1988), incorporated herein by reference]. FIAU-MP was obtained by selectively phosphorylating 5'-OH group according to the following procedure.

To a mixture of phosphoryl chloride (2.58 ml), pyridine (2.44 ml), water (0.317 ml) and acetonitrile (6.3 ml), which was maintained at 2° C. with stirring, 2.34 g FIAU was added, after which the mixture was maintained at 2° C. for 1 h. LiOH (60 ml, 1 M) was added to the mixture to quench the reaction. The mixture was left standing overnight, and the Lithium phosphate precipitate was collected. After the filtrate was concentrated to about 10 ml, 40 ml EtOH was added to precipitate the product. The product was collected by centrifugation and subjected to fractional precipitation to remove FIAU-3',5'-diphosphate. The collected product was redissolved in water, and ethanol was added to the solution dropwise until the solution became cloudy. The cloudy solution was immediately centrifuged and the supernatant was mixed with 40 ml ethanol to precipitate the product. 1.1 g FIAU monophosphate was obtained, free of diphosphate.

B. Preparation of EDA-P-FIAU

FIAU-monophosphate (P-FIAU, 1.54 g (3.4 mmol)) and 323 ul (3.4 mmol) ethylenediamine were dissolved in 8.5 ml deionized water, and the pH was adjusted to 6.3 using 6M HCl at 50° C. The reaction was initiated by adding 1.3 g (2×3.4 mmol) EDC. The reaction was stirred at 50° C. for 2 hours before an additional 0.34 g EDC was added. The reaction was kept stirring at 50° C. for another hour, and HPLC showed the reaction was complete. The mixture was adjusted to pH to 12 using 5 M NaOH and stirred for 0.5 h. EtOH (40 ml) was added to precipitate the product, which was collected by centrifugation and subjected to water-EtOH precipitation two more times. HPLC showed that purity was about 80%. A fraction of the product (about 50 mg) was loaded to C18 Sepak column and eluted with water. The fraction containing the product was pooled and rotervaped. The purified product had more than 97% purity and $^1$H-NMR was obtained.

Example 13

Ethylene Diamine AZT monophosphate (EDA-P-AZT)

Preparation of P-AZT

A 100 ml round bottom flask with stir bar was charged with 44 ml acetonitrile, and 13.96 ml POCl$_3$. The mixture was cooled to 0° C., and 1.34 ml de-ionized water was added, followed by 12.1 ml pyridine. After stirring 2 min., 10.0 g AZT was added. The mixture was stirred for 60 min. at room temperature, cooled back down to 0° C. on an ice bath, and added to 200 ml ice cold 1 M LiOH. The pH was monitored, and 4 M LiOH was continuously added until the pH stabilized to pH 8–9. The solution was stirred overnight, and a final pH adjustment to pH 8–9 was made. The precipitate that formed was filtered off using a coarse glass fritted funnel, 150 ml, and the precipitate was washed twice with 25 ml de-ionized water. The filtrate and water washes were combined and evaporated at 40° C. Crude yield: 76 g, yellow solid. To the residue was added 100 ml EtOH and 400 ml MeOH. After heating to a gentle boiling, the solid was collected on a medium glass frit funnel, and washed successively with 2×100 ml acetonitrile. The product was dried in vacuo. Yield: 12.15 g, yellowish solid. The solid was taken up in 50 ml de-ionized water, and 0.5 g activated carbon was added. The carbon was removed by 0.2 μm filtration, and Amberlite IR-120H+ resin was added until pH 2.15 was reached. The resin was filtered off using a 0.2 μm filter, and 0.5 g activated charcoal was added. The charcoal was removed by 0.2 μm filtration, and the solution was lyophilized. Yield: 11.45 g, yellow solid. CZE of this material indicates it is 96% pure. IR: 2112 cm$^{-1}$, strong. To further purify this material, 4 g of the product was sonicated with 50 ml ethanol for 60 min. The solid was collected by centrifuge and dried under vacuum. Yield: 2.65 g. Anion exchange HPLC indicates the product is 99.2% pure.

Preparation of EDA-P-AZT

To 2.22 g ethylenediamine dihydrochloride in 8 ml de-ionized water was added 4.00 g P-AZT and 0.732 ml ethylenediamine. The pH was adjusted to 6.3 by adding 6 M HCl (about 1.4 ml). The mixture was heated to 50° C., and 5.2 g EDC was added to the stirring mixture. After stirring for 60 min., the mixture was cooled to room temperature, and the water was removed in vacuo. The remaining solid residue was triturated with 50 ml EtOH, and 75 ml acetonitrile was added. The solid was collected on a Buchner funnel (Whatman #2 filter paper), and washed with 25 ml acetonitrile. The solid was suspended in 50 ml acetonitrile, and again collected on the Buchner funnel (fresh Whatman #2 filter paper). The solid was dried under vacuum. The solid was dissolved in 4 ml de-ionized water, and the solution was cooled on an ice water/bath. To the crude product solution was added 5 M LiOH until pH 11.15 was reached. The solution was 0.8 μm filtered and added dropwise to 100 ml EtOH. To the ethanolic solution was added 200 ml acetonitrile. The precipitate that formed was collected on a Buchner funnel (Whatman #2 filter paper). The solid was dried under vacuum. Yield: 1.8 g. Anion exchange HPLC: 89.6% pure. TLC: Merck Silica Gel-60, 0.5 mm, cat 5744; single spot, ratio of fronts=0.23, EDA is not detected down to 1 mol %.

Example 14

Ethylene Diamine ddA monophosphate (EDA-P-ddA)

A. Preparation of Dideoxyadenosine Monophosphate (ddAMP)

To a stirred mixture of dideoxyadenosine (ddA) (100 mg) in 4 mL of trimethylphosphate was added 100 μL of phosphorous oxychloride. After stirring for 1 hour, the reaction mixture was poured into a solution (5 mL) of 4N LiOH after stirring for 1 hour, the Li$_3$PO$_4$ was filtered off and the water removed under vacuum leaving residue of trimethyphosphate and product. The solid collected by filtration and redissolved in 2 mL of water. Undissolved material was removed by filtration and the product precipitated by addition of 10 mL of ethanol. After filtration the precipitation was repeated yielding 27 mg of ddAMP dilithium salt based on CZE retention time. The product may also be obtained by ion exchange chromatography of the initial precipitate.

B. Preparation of dideoxyadenosine-5'-(2-aminoethyl) phosphoramidate

The pH of a stirred mixture of ddAMP dilithium salt (100 mg) and 80 mg of ethylenediamine hydrochloride in 100 μL of water is adjusted to pH=6.3 by careful addition of ethylene diamine. The solution is then heated to 50° C. and 160 mg of EDC is added. After stirring for 1 hour, the water is evaporated in vacuo and 4 mL of ethanol is added. The precipitate is collected and redissolved in water (200 μL) and the pH adjusted to 11.5 with 4 N LiOH. The solution is then poured into 4 mL of ethanol and the precipitate (dideoxyadenosine-5'-(2-aminoethyl)phosphoramidate as the lithium salt) collected.

Example 15

Ethylene Diamine-Ribavirin monophosphate (EDA-P-Riba)

A. Preparation of Ribavirin 5'-Monophosphate

The manufacture and synthesis Ribavirin (ICN Pharmaceuticals, Costa Mesa Calif.) are described in U.S. Pat. No. 4,211,771, incorporated herein by reference. A dry 1 L ml 3-neck round bottom flask, equipped with a stir bar, gas inlet adapter, and thermometer, was charged with 50 g Ribavirin (0.204 moles), 500 ml trimethyl phosphate, and 0.367 ml de-ionized water (0.0204 moles). The mixture was cooled under nitrogen with an ice/water bath. When the temperature reached 10° C., 23.3 ml phosphorous oxychloride was added, the flask was removed from the ice bath, and the mixture was stirred under nitrogen. After 30 min., the flask was cooled in the ice/water bath. When the temperature reached 10° C., the mixture was poured into a 2 L beaker containing 1000 ml ice water. The pH was adjusted to pH=9.0 using a 4 M LiOH and the mixture was stirred overnight. After final adjustment to pH 9, the white precipitate that has formed is filtered away using a 0.2 mm filter. The mixture was evaporated at 40° C. under reduced pressure to 1 L. The solution was added to 1 L hot ethanol dropwise. The white precipitate was collected on a 2 L glass fritted funnel, coarse grade, washing the solid with two 100 ml portions of ethanol, re-suspending the solid each time. The product was dried under vacuum overnight, yield: 89 g. The solid was dissolved in 200 ml de-ionized water, and 5 g activated carbon was added. The mixture was filtered through a 0.2 mm filter, washing the carbon with 50 ml de-ionized water. The filtered solution was added dropwise to 1200 ml hot ethanol The mixture was cooled to room temperature, and the precipitate was collected on the 2 L glass fritted funnel. The solid was washed with 2×100 ml ethanol in the funnel, and dried under vacuum. Yield: 66.6 g. The dried product was dissolved in 200 ml de-ionized water. Amberlite IR-120 H.C.P. resin (H+ form) was added until the pH of the mixture reached pH=2.18. The resin was filtered off using a 0.2 mm filter, and the final solution was lyophilized. Yield: 54.8 g (0.160 moles), 78.5%, Ribavirin 5'-monophosphate. Elemental analysis indicates the product contains 1 mole water/mol ribavirin 5'-monophosphate.

B. Preparation of Ribavirin 5'-(2-aminoethyl) phosphoramidate (EDA-P-Riba)

A tared 1 L 24/40 standard taper flask with a stir bar was charged with, in order, 10 g ribavirin 5'-monophosphate monohydrate (29.4 mmoles) (from A, above), and 10 ml de-ionized water. The solution was cooled on an ice bath, and 10 ml 1,2-ethylenediamine (150 mmoles) was added, followed by 6 M HCl until pH=6.3 was obtained (about 40 ml). The flask was placed in a water bath heated to 50° C., and 30 g EDC (156 mmoles) was added. After stirring for 30 min., another 10 g EDC (52.1 mmoles) was added, followed by stirring for 60 min. at 50° C. Most of the water was removed in vacuo using the rotoevaporator until a total weight of 82 g remained. The resulting thick oil was triturated with 400 ml EtOH. The precipitate that formed was collected on a glass scintered Buchner funnel (coarse) under nitrogen. The solid was re-suspended in 400 ml fresh ethanol, collected on the Buchner funnel, and dried under vacuum. Yield: 11.93 g, white solid. The dried solid was dissolved in 10 ml water and cooled on an ice bath. To this mixture was added cold 4 M LiOH until pH 11.5 was reached. The solution was 0.8 mm filtered through a syringe filter into 400 ml ethanol dropwise. The precipitate was collected on a porcelain Buchner funnel (Whatman filter paper #54), washed with ethanol, and dried under vacuum. Yield: 5.95 g, 97.3% pure by anion exchange HPLC analysis. The ethanol filtrate from the LiOH/EtOH precipitation was concentrated under reduced pressure at 40° C. to 50 ml. The precipitate that formed was collected by filtration, washed with ethanol, and dried under vacuum. Yield: 1.40 g, 97.9% pure by anion exchange HPLC analysis. The combined yield is 7.35 g, (17.6 mmoles), 60.2 mol % from ribavirin 5'-monophosphate monohydrate. NMR analysis shows 1 mole EtOH/mol ribavirin 5'-(2-aminoethyl) phosphoramidate. TLC analysis (Silica Gel 60, Merck, F254, 7:2:1 i-PrOH/water/28% ammonia) indicates the ethylenediamine content is less than 0.27% by weight (1.8 mole %).

Example 16

Ethylene Diamine-araA monophosphate (EDA-P-araA)

To a mixture of ethylene diamine (2.5 mL), adenosine 5-monophosphate (10 g), and 1-hydroxybenzotriazole (HOBt, 3.7 g) 1-ethyl-3-(3-dimethylaminopropyl) carbodiimide (EDC, 15 g) over 3.5 h at 40° C. in 4 portions. The water was removed under vacuum and the product triturated with 50 mL of 2:1 $CH_3CN$/MeOH. The solid was washed with an additional 100 mL of acetonitrile and dried under vacuum at 50° C. The solid was passed through a 2.5 cm×25 cm column containing 100 mL of wet volume Amberlite IR-120 (Na form) ion exchange resin. The fractions containing the product, ethylenediamine-araAMP (EDA-P-araAMP, first 250 mL) were combined and the water was removed under vacuum. The product was again triturated with 2:1 acetone/MeOH, and washed with 100 mL of acetone. The product was dried under vacuum for 2 h at 50° C. Yield: 8.2 g.

Example 17

HES-IPA-Hexane Diamine-(HES-IPA-HDA)

A. Preparation of HES-IPA-Br

HES (250 g) is dissolved in 874 mL water. $Zn(BF_4)_2$ (62.5 g) is added and the reaction transferred to a jacketed vessel. Oil, circulating at 130° C. is circulated through the jacket. When the contents reach 100–110° C., 1250 mL of epibromohydrin is added. The mixture is stirred for 90 minutes and the temperature maintained. The mixture is exhaustively ultrafiltered. The retentate is lyophilized. Elemental analysis of bromine: 2–5% bromine by weight, or 0.25–0.5 meq/g.

B. Preparation of HES-IPA-HDA The product (HES-Br, 15 g) is slurried into 80 mL DMF. Hexamine diamine (100 g) is heated to melting, filtered to remove particulates, and added to the slurried HES-Br. The mixture is heated for 5–10 min at 60° C. to dissolve all reactants, then maintained at 40° C. for 4 h. The product is precipitated with ethanol, washed with ethanol, and redissolved in water. It is ultrafiltered four times with the addition of about 5 volumes of water per volume of concentrate, using a 3000 MW cutoff ultrafiltration filter. The recovered material is lyophilized. The amine content is determined by ninhydrin assay.

Example 18

HES-IPA-Butane Diamine (HES-IPA-BDA)

HES-IPA-Br (from Example 18A, 22 g) is mixed with molten butanediamine (82 g) in DMF for 4 h at 75° C. Water (50 mL) is added and the mixture cooled in an ice bath. Chloroform (500 mL) is added in separatory funnel and the material shaken and allowed to settle. The top aqueous layer is saved and extracted with 200 mL, then 100 mL of chloroform. A final extraction is performed with 200 mL ethyl ether. The aqueous portion is evaporated and redissolved in water. It is then ultrafiltered four times with the addition of five volumes of water per volume of concentrate using a 3000 Dalton molecular weight cutoff ultrafiltration membrane. The completeness of the ultrafiltration process is confirmed by testing the amine content of the filtrate. The retentate is vacuum dried. The product is analyzed for amine content by ninhydrin assay. There are 0.4–0.5 meq of butanediamine per gram of product.

Example 19

4 aminophenylethylamine-araA monophosphate (4PDA-P-araA)

AraAMP (378 g, 1 mmol) and 4 aminophenylethylamine (197 μL, 1.5 mmol) are dissolved in 1 mL deionized water, and the pH is adjusted to 6.3 using 6M HCl at 50° C. The reaction is initiated by adding 384 mg EDC. The reaction is monitored by HPLC until completion. If it is not completed within 2 h, an additional 80 mg EDC is added. The reaction is stirred at 50° C. for another hour. EtOH (20 mL) is added to precipitate the product. The product is characterized by TCL, HPLC and NMR.

Example 20

Ethylene Diamine-Adenine diphosphate (EDA-2P-Ad)

Ethylenediamine(0.225 g) was dissolved in 2 ml of DI water and stirred adenine diphosphate sodium salt (1 g, ADP, Sigma Chemicals) was added and stirred until completely dissolved. HCl (0.5 ml, 6M) was added dropwise. The solution was adjusted pH 6.3 with 6M HCl and heated to 50° C. with stirring. EDAC(1 g) was added and stirred at 50° C. for 1 h then 0.25 g of EDAC was added and stirred at 50° C. for 30 min. 20 ml DMF was added and placed in 0–5° C. for 16 h.

The precipitate was collected and dissolved in 2 ml of DMF. The solid was filtered and redissolved in 1 ml of DI water. 10 ml of DMF was added and the precipitate was filtered and washed with ethanol. Yield 0.93 g.

Example 21

Ethylene Diamine-Adenine triphosphate (EDA 3P-Ad)

Ethylenediamine (0.253 ml) was dissolved in 2 ml of DI water and stirred. ATP (1.18 g, ATP disodium salts, from Sigma) was added and stirred until completely dissolved. The solution was adjusted to pH 6.3 with 7.5 M HCl and heated to 50° C. with stirring. EDAC(1 g) was added and the reaction was stirred at 50° C. for 1 h). EDAC (0.25 g) was added and the reaction stirred at 50° C. for 30 min. DMF (20 ml) was added and the reaction was chilled to 0–5° C. for 16 h. The precipitate was filtered and washed by DMF and dried. Yield 1.4 g.

Example 22

Polyglutamate-EDA-P FUDR

To a reaction vessel, 70 mg of 5 M NaOH solution and 7.9 mL of distilled water were combined. While stirring, 11.5 mg of HOBT was added and the solution was heated to 50° C. The pH was adjusted to 5.5, and 25 mg of poly-L-glutamic acid was added. EDA-P-FUDR (110 mg, from Example 9) and 265 mg of EDAC was added to the stirring solution. The reaction was continued under stirring at 50 C. for 90 minutes then 16 hours at ambient temperature.

Measurements of the molecular weight distributions were made with an Ultrahydrogel 250 column. The injection volume was 20 μl. The mobile phase was the 20 mM phosphate buffer (pH 7.3) with a flow rate of 0.4 ml/min. Mw (kDa) 19.832; Mn (kDa) 13.634; Mp (kDa); 15.849; Mw/Mn1.45.

Example 23

Dextran (40 kDa)-CM-EDA

A mixture of Dextran (T40) CM (Na salt; 50.27 g, 0.0709 mol COO—) prepared as described in Example 4, 1,2-ethylenediamine (50.1 g, 0.835 mol), 1-hydroxybenzotriazole hydrate (68.5 gl 0.507 mol), N,N,N',N'-tetraethylethylenediamine (100 g) in $H_2O$ (125 mi,) was cooled in an ice bath while being neutralized with concentrated HCl to pH 6.9. After warming to room temperature, 1-ethyl-3-(3-dimethylaminopropyl) carbodiimide hydrochloride (96 g, 0.50 mol) was added and the reaction mixture was stirred for 23 h. The reaction mixture was mixed with $H_2O$ (700 mL) and the product was isolated by ultrafiltration with a 3 kDa cut-off filter (Diaflo® YM3, Amicon, Beverly, Mass.). The retentate was washed with 0.1 M NaCl (2×700 mL) and $H_2O$ (6×1500 ml). The product was lyophilized to yield an off-white solid. Yield: 46 g. Elemental analysis: 1.69 wt % N, 0.60 mmol ethylenediamine/g conjugate.

Example 24

Dextran (40 kDa)-CM-EDA-P-FUDR

An aqueous solution (5 mL) of 2'-deoxy-5'-phosphate-5-fluorouridine FUDR-MP Li salt (0.286 g, 0.85 mmol, P-FUDR prepared as described in Example 9A), Dextran (T40) CM-EDA from Example 23 (1.31 g, 0.79 mmol —NH2) and 1-ethyl-3-(3-dimethylaminopropyl)-carbodiimide hydrochloride (0.60 g, 3.1 mmol) were stirred at 48–50° C. for 1.5 h. At room temperature, the solution pH was 8.4. The product was isolated by ultrafiltration with a 30 kDa cut-off filter (Diaflo®, PM30, Amicon, Beverly, Mass.), washed with 0.1 M NaCl (50 ml) and $H_2O$ (7×50 mL). Lyophilization yielded a white crystalline solid. Yield: 1.25 g. Elemental analysis: 0.53 wt % P, 0.17 mmol FUDR-MP/g conjugate.

Example 25

Dextran (70 kDa)-CM-EDA-P-araC

1-Hydroxybenzotriazole hydrate 68 mg (0.504 mmol, HOBt) was dissolved in 2.5 mL distilled water and pH was adjusted to 5.5 using 5M NaOH at 50° C. Dextran (T70)-CM 200 mg (from Example 5) and 126 mg (0.346 mmol) of EDA-P-araC (Example 10) were added. EDC (320 mg, 2.56 mmol) was added after all the reagents were dissolved. The reaction was maintained at 50° C. for 1.5 hour with stirring, and then overnight at room temperature. The reaction mixture was diluted to 50 ml with water and ultrafiltered twice against a YM3 membrane (Amicon, Beverly Mass.). Sodium chloride (0.66 g) was added to 50 ml water, and this solution was used for third ultrafiltration, followed by 5 more ultrafiltration against water. After the last ultrafiltration, the residue was filtered through a 0.22 μm filter and lyophilized.

Yield, 143 mg of white powder. EDA-P-araC loading: 0.179 mmol/g. $M_w$ 69 K

Example 26

Dextran CM-4PDA

A 1.0 ml solution containing 45.3 mg (0.335 mmol) HOBt and 135 mg dextran(T10)-CM (from Example 1) is added to a reaction vial. The pH is adjusted to 5.5 using 5 M NaOH at 50° C., followed by adding 4-aminophenylethylamine (44 μL, 0.335 mmol). EDC (213 mg) is then added to start the reaction. The reaction is maintained at 50° C. for 1.5 hour with stirring, and then overnight at room temperature. The reaction mixture is diluted to 50 mL with water and ultrafiltered twice against a YM3 membrane. Sodium chloride (0.67 g) is added to 50 mL water, and this solution is used for third ultrafiltration, followed by 5 more ultrafiltrations against water. After the last ultrafiltration, the residue is filtered through a 0.22 μm filter and lyophilized.

Example 27

Dextran(70 kDa)CM-EDA-P-ddA

Dideoxyadenoine-5'-(2-aminoethyl)-phosphoramidate (100 mg, from Example 14) and Dextran T-70 (1000 mg, from Example 5) are added to 1 mL of water and the mixture is stirred until complete dissolution. HOBt (50 mg) is weighed out and ~2/3 is added to the reaction. After dissolution the pH is measured and additional HOBt added until the pH=5.65. The reaction is then placed in a 55° C. water bath and 250 mg of EDAC is added. For the first ten minutes of the reaction the pH is maintained at <6.25 by the careful addition of 6N HCl then stirred for two hours.

The reaction mixture plus 3×5 mL washes are transferred to an Amicon Ultrafiltration cell with a YM3 3K MWCO membrane. NaCl (200 mg) is added and the solution diluted to 50 mL. The solution is then filtered down to 10 mL and the process (without NaCl) repeated 5 times. After the final filtration, the retentate is lyophilized to the conjugate as a white solid.

Example 28

Dextran(70 kDa)CM-EDA-P-Ribavirin

A solution of 20 ml de-ionized water, 2.00 g Dextran(70 kDa)-CM (from Example 5), 1.93 g EDA-P-riba (from Example 15), and 0.67 g HOBt was heated to 50° C. The pH was measured, and additional HOBt was added until pH 5.66 was reached (0.5 g additional HOBt added). To the stirring solution was added 3.2 g EDC. The mixture was stirred at 50° C. for 60 min., and then stirred at room temperature for 16 h. The mixture was next diluted to 200 ml with de-ionized water and repeatedly ultrafiltered with de-ionized water against an Amicon YM-3 3000 MWCO ultrafiltration membrane in a 200 ml ultrafiltration stirred cell. After the first concentration, 2.0 g NaCl was added. After the fifth concentration, the retentate was 0.2 μm filtered and lyophilized. Yield: 1.98 g. UV: λ max=191 nm, A214 nm=0.4018 for a 0.100 mg/ml solution; ribavirin loading based on measured $\epsilon$=10455 $M^{-1}$ at 214 nm for ribavirin=0.4013 mmol/g. LLS-HPLC: Mw=187.25 K, Mn=101.25 K, Mw/Mn=1.85, Mp=229.09 K; retention time=13.85 min. for 0.4 ml/min. flow rate on the Waters Ultrahydrogel 250 column, 7.8×300 mm.

Example 29

Dextran (70 kDa))-HA-EDA-P-araC

A dextran hexanoic acid derivative utilizing a 70 kDa dextran was obtained from CarboMer (Westboro, Mass.). EDA-P-araC (from Example 10) is reacted with 200 mg of Dextran-HA as described in Example 25.

Example 30

Dextran (T10)-IPA-Hydrazide-araAMP

A. Preparation of Dextran (T10)-IPA-Hydrazide

Dextran(T10) (10 g) is dissolved in 25 mL of water. Ten mL of a 25% solution of $Zn(BF_4)_2$ is added, followed by 50 mL of epibromohydrin. The mixture is heated to 100–110° C. for 3 hours, with 25 mL of epibromohydrin added after the first hour, and an additional 20 mL epibromohydrin is added after the second hour. The product is precipitated with 700 mL cold acetone, washed with 25 mL ethyl acetate, dissolved in water, precipitated with 700 mL cold ethanol and washed with 25 mL ethyl acetate.

The product (5 g) is dissolved in 15 mL borate (4.5 mL of 1M borate solution in 10.5 mL water). Ten grams of hydrazide is added and the mixture stirred for 12 h at room temperature. Product is precipitated in acetone, dried, redissolved in water, precipitated in ethanol, and dried. Yield, approximately 5.8 g of product, which is tested for halogens by flame test; the amine content is assessed by titration win 0.1N NaOH.

B. Preparation of Dextran (T10)-IPA -Hydrazide-araAMP

Dextran (T10)-IPA-Hydrazide (0.6 g) and araAMP (1 g, 2.9 mmoles) are dissolved in 20 mL water. The pH is adjusted to 7.5 with NaOH. 1-ethyl-(3,4-dimethylaminopropyl)carbodiimide (EDAC, 1 g, 5.2 mmoles) is added and the mixture is maintained in the dark at room temperature for 64 h. The product is filtered through a 0.45 micron filter, precipitated with 200 mL ethanol, redissolved and ultrafiltered using a 3000 dalton molecular weight cutoff filter. The product is again precipitated with 200 mL ethanol.

Example 31

Dextran(70 kDa)CM-EDA-P-AZT

A solution of 20 ml de-ionized water, 2.0 g Dextran(70 kDa)-CM, 2.03 g EDA-P-AZT, and 0.67 g HOBt was heated to 50° C. The pH was measured, and additional HOBt was added until pH 5.61 was reached (0.84 g additional HOBt added). To the stirring solution was added 3.2 g EDC. The mixture was stirred at 50° C. for 60 min., and then stirred at room temperature for 16 h. The mixture was next diluted to 200 ml with de-ionized water and repeatedly ultrafiltered with de-ionized water against an Amicon YM-3 3000 MWCO ultrafiltration membrane in a 200 ml ultrafiltration stirred cell. After the first concentration, 2.0 g NaCl was added. After the fifth concentration, the retentate was 0.2 μm filtered and lyophilized. Yield: 2.27 g. UV: λ max=267 nm, A267 nm=0.3843 for a 0.100 mg/ml solution; AZT loading based on measured $\epsilon$=9787 $M^{-1}$ for AZT=0.399 mmol/g. LLS-HPLC: Mw=165.66 K, Mn=95.21 K, Mw/Mn=1.74, Mp=206.54 K; retention time=13.94 min. for 0.4 ml/min. flow rate on the Waters Ultrahydrogel 250 column, 7.8×300 mm.

Example 32

Dextran (T10) CM-4PDA-P-araA

AraAMP (P-araA, 378 mg, 1 mmol) and Dextran (10 kDa)-CM4-PDA (from Example 26) are dissolved in Deionized water. The pH is adjusted to 6.3 using 6M HCl and the solution is warmed to 50° C. EDAC (384 g) is added to the reaction and stirring is maintained for 2 hours. An additional 80 mg of EDAC is added, and the reaction stirred at 50° C. for another 1 hr. The solution is diluted with water (50 mL) and ultrafiltered twice using a YM3 membrane. Sodium Chloride (0.67 g) is added to 50 mL water, and this solution is added to the third ultrafiltration. The solution is ultrafiltered 5 times more against water, filtered through a 0.22 $\mu$m filter and lyophilized.

Example 33

Dextran-lysine-P-araA

The lysine ester-araAMP (from Example 8) is coupled to a carboxymethyl dextran (Dextran (T10)-CM from Example 1) by the formation of an amide bond between a carboxyl from the polysaccharide and the free (primary) lysine of lysine. The chemistry used for the coupling of EDA-P-araA to Dextran (T40) CM, which uses EDAC and is catalyzed by HOBT, is used to couple the Dextran-CM to Lysine-P-araA. Treatment of the final product under alkaline conditions (such as dilute NaOH or bicarbonate buffer) hydrolyzes the ester to yield a carboxyl, while leaving the amide and phosphoramide bonds unaltered.

Example 34

Dextran(10kDa)CM-EDA-P-FIAU

EDA-P-FIAU (from Example 12) is coupled to Dextran (10 kDa)-CM (from Example 1) according to the method of Example 28.

Example 35

Poly-Glu(25 kDa)-EDA-P-araA

A 250 mg sample of polyglutamic acid, sodium salt (Sigma, cat. P-4761, Mw=25 kDa by LLS) was dissolved in 12.5 ml de-ionized water. To this solution was added in order 85 mg N-hydroxybenzotriazole and 185 mg EDA-P-araA (Code 4045, the conjugate of ethylenediamine and araAMP). The pH was measured and found to be pH 5.53. The solution was heated to 50° C., and 400 mg 1-(3-dimethylpropyl)-3-ethylcarbodiimide hydrochloride was added. After 1 hour heating at 50° C., the solution was removed from the heat source and stirred 16 h at room temperature. The mixture was diluted to 200 ml and ultrafiltered against a YM-3 filter (MWCO 3000, Amicon). After three concentrations, the retentate was filtered through a 0.2$\mu$m filter, and lyophilized. Yield: 70 mg. The araAMP loading based on UV analysis of the araAMP chromophore was 0.81 mmol araAMP/g. The HPLC retention time of the conjugate on a Waters UHG 250 size exclusion column (20 mM phosphate buffer, pH 7, flow rate 0.4 ml/min) was 17.5 min. (BSA=16.1 min., araAMP=20.23 min.).

Example 36

HES(75 kDa)-IPA-EDA-P-araC

To a solution of 0.4 g cytosine 5'-monophosphate arabinofuranoside, 0.75 g of HES-IPA-EDA (from Example 7) in 3 ml de-ionized water was added enough N,N,N',N'-tetraethyl-ethylenediamine to bring the solution to pH 6.27 (about 0.1 ml). The mixture was heated to 50° C. and 1.76 g 1-(3-dimethylaminopropyl)-3-ethylcarbodiimide was added. The solution was stirred at this temperature for 50 min., removed from the heating source, and stirred overnight at room temperature. The reaction mixture was diluted to 180 ml and ultrafiltered against a YM-3 Amicon ultrafiltration membrane in an Amicon 200 ml ultrafiltration stir cell. After the first concentration, 0.75 g NaCl was added. After the fifth concentration, the retentate was filtered through a 0.2 $\mu$m filter, and lyophilized. Yield: 0.6 g, white solid. The araCMP loading based on UV analysis of the araCMP chromophore was 0.54 mmol araCMP/g. The HPLC retention time of the conjugate on a Waters UHG 250 size exclusion column (20 mM phosphate buffer, pH 7, flow rate 0.4 ml/min) was 16.2 min. (BSA=16.1 min., araAMP=20.23 min.).

Example 37

Dextran-Amine

Dextran (10 g) is dissolved in water (100mg/ml) and the pH is adjusted 11 with 2 M sodium hydroxide. The solution is cooled to 4° C. Cyanogen bromide (1 g) is dissolved in dimethylformamide, and added to the solution of dextran with vigorous stirring. The pH is adjusted to 11 with sodium hydroxide and maintained at pH 11 by the controlled addition of more sodium hydroxide. After 10 minutes sufficient ethanol is added to precipitate the dextran, which is collected by centrifugation and redissolved in phosphate buffer, pH 7.5. An amino containing derivative (such as ethylene diamine) is added to the cyanogen activated dextran and allowed to react for 5 hours at 25 C. The reaction mixture is dialyzed against water and lyophilized.

Example 38

HES-CM-EDA-P-araA

HES-CM (3 g, from Example 2) was dissolved in 5 mL of DI water and stirred. HOBT (1 g) was added and the mixture was adjusted to pH 6.3 with 6M NaOH, then heated to 50° C. under stirring. EDA-P-araA (2.3 g, from Example 16) was added, the pH was adjusted to 6.3 at 50° C. with 6M HCl. EDAC-HCl (4.8 g) was added and the solution was stirred at 50° C. for 1 hr.

The reaction mixture was transferred to an ultrafiltration filter and diluted to 160 mL with DI water and 20 mL of saturated NaCl. The mixture was filtered against a 3000 MWCO membrane, When the solution was concentrated to 5–8 mL, the contents were reconstituted with 10 mL saturated NaCl solution and 160 mL of DI water; this procedure was repeated two more cycles, and lyophilized. Yield: 3.8 g, MW 22,150; Mn 66056; loading 0.76 mmol araA/g.

Example 39

Dextran (70 kDa)CM-EDA-P-ACV

EDA-P-ACV(2 g, ~91%, Example 11) was suspended in 20 ml of DI water and stirred. HOBT(0.8 g) was added and heated to 55° C. with stirring. Dextran(70 kDa)-CM (2.2 g, Example 5) was added and adjusted pH5.6 at 55° C. with 3M HCl. EDAC.HCl (2.2 g) in 2 ml of water was added over 2 min and stirred at 55° C. for 40 min. Another 1.5 g of EDAC in 1 ml of water was added and stirred at 55° C. for 2 h and room temperature for 48 h.

The reaction mixture was centrifuged and the supernatant was diluted to 160 ml with DI water and filtered against 3000 MWCO membrane. After two cycles of filtration with NaCl (150 ml DI water and 10 ml of saturated NaCl) and 4 cycles with DI water, the final content was filtered through 0.2 um filter and lyophilized to give 2.25 g conjugate, Loading 0.14 mmol/g, Mw 304220, Mn 117820, Mp 272270, Mw/Mn 2.6.

Example 40

Dextran (70 kDa)CM-EDA-araA

1-Hydroxybenzotriazole hydrate 68 mg (0.504 mmol, HOBt) was dissolved in 2.5 mL distilled water and pH was adjusted to 5.5 using 5M NaOH at 50° C. Dextran (T70)-CM 200 mg (from Example 5) and 148 mg of EDA-P-araA (Example 16) were added. EDC (320 mg, 2.56 mmol) was added after all the reagents were dissolved. The reaction was maintained at 50° C. for 1.5 hour with stirring, and then overnight at room temperature. The reaction mixture was diluted to 50 ml with water and ultrafiltered twice against a YM3 membrane (Amicon, Beverly Mass.). Sodium chloride (0.66 g) was added to 50 ml water, and this solution was used for third ultrafiltration, followed by 5 more ultrafiltration against water. After the last ultrafiltration, the residue was filtered through a 0.22 μm filter and lyophilized.

Example 41

Dextran (T10)-CM-EDA-P-araA

Dextran (T10)-carboxymethyl (from Example 1) was conjugated to EDA-P-araA (Example 16) according to the methods in Example 40. The conjugate was designated Dextran(10 kDa)-CM-EDA-P-araA.

Example 42

Antiviral Activity Of Macromolecular Prodrugs In Cell Culture

The antiviral activities and cytotoxicity of a macromolecular prodrug of Dextran-araA made according to the teachings in Example 40 and the parent nucleoside analog araA were evaluated using 2.215 cells (obtained from transfection of the Hep G2 human hepatoblastoma cell line with HBV) as described by Korba and Gerin (Korba B E, Gerin J L., Antiviral Research 1992; 19:55–70.) It is standard system widely used to compare the safety and efficacy of drugs for the treatment of HBV. The data for β-L-FTC, a nucleoside analog with pharmacological properties similar to Lamivudine (3TC), in the same system are shown for comparison. Lamivudine is a recently developed nucleoside analog that has been approved by the U.S. FDA for the treatment of HIV and has shown promise in extensive clinical trials against HBV Briefly, the test compounds were added to confluent cultures of 2.2.15 cells every 24 hours for nine consecutive days in fresh culture media (RPMI 1640 with 2% fetal bovine serum, Gibco Inc., Grand Island N.Y. U.S.A.). The amount of extracellular HBV virion DNA and intracellular HBV replication intermediates were determined using quantitative blot hybridization analyses (dot, Southern and northern blots, respectively, Korba B E, Gerin J L., Antiviral Research 1992; 19:55–70; Korba B E, Milman., Antiviral Research 1991; 15:217–228).

Efficacy was determined by the concentrations of agent giving 90% inhibition of viral replication ($EC_{90}$) as measured in changes of HBV virion DNA and replicative intermediates. Cytotoxicity caused by the agents was measured by the uptake of neutral red dye. The cytotoxic concentration ($CC_{50}$), was considered to be the concentration at which 50% of the cells took up due the dye. The selectivity index (SI, $CC_{50}/EC90$) is measure of drug toxicity in relation to drug efficacy. The results are shown in Table 3.

TABLE 3

Effect Of Macromolecular Prodrugs On HBV Replication In 2.2.15 Cells

| Compound | $CC_{50}$ μM araA eq | $EC_{90}$ μM araA eq | SI ($CC_{50}/EC_{90}$) |
|---|---|---|---|
| araA | 188 ± 20 | 17 ± 1.9 (25 ± 2.1) | 11 (7.5) |
| Dex(70 kDa)-CM-EDA-P-araA (Example 40) | >3000 | 0.7 ± 0.1 (1.3 ± 0.2) | >4200 (>2300) |
| β-L-FTC* | 746 | 1.1 (0.39) | 678 (1913) |

Extracellular DNA: No Parentheses; Intracellular RI DNA: Parentheses ()
*Schinazi et al. Antimicrob. Agent Chem (1994) 38, 2172.

The results in Table 3 show that the prodrug had a >20 fold increase in the $EC_{90}$ value indicating markedly enhanced antiviral activity, and >15-fold decrease in the $CC_{50}$ values, indicating reduced cytotoxicity over the parent nucleoside (araA). The difference in behavior between the macromolecular prodrug of araA and araA implies that the prodrug is stable in the culture media traverses the cell membranes, and releases a metabolically active and highly beneficial antiviral agent. Thus, when araA is used to synthesize a macromolecular prodrug of the invention, it is remarkably transformed from a drug with an SI of about 10 to one with an SI of over 1000. Similarly, the prodrug showed a 4 fold decrease in cytotoxicity over β-L-FTC. Thus, when araA is synthesized into a macromolecular prodrug, it is transformed from a compound with an SI smaller than β-L-FTC to one with an SI greater than β-L-FTC. This infers that macromolecular prodrugs of nucleotide analogs can improve the safety and efficacy of nucleotide analogs made from nucleoside analogs by overcoming poor transport into or poor phosphorylation inside cells.

Example 42

Stability/Releasability Assays of Macromolecular Prodrugs

The macromolecular prodrug from Example 41 was tested for stability of the prodrug in biological fluids (human plasma) and releasability of the nucleotide in tissue extracts (rat liver extracts) as follows.

Preparation of Tissue Extracts

Freshly excised rat livers (20 g) were mixed with phosphate buffered saline (PBS, 15–20 mL) and cooled to 0°. While cooled in an ice-water bath, the liver tissue was disrupted with a Branson Model 184V Sonicator using repeated 10 sec pulses until only 1–2 g of off-white solid remained. The PBS solution was replaced several times during the course of this treatment. The combined PBS extracts (~50 mL) were centrifuged with a Sorval Model SC2-B centrifuge equipped with a SS34 rotor at 19000 rpm (ca. 28,000 g) at ~4° for 1 h. The clear supernatant was filtered through successive 0.8, 0.45 and 0.22 mm filters. The final filtrate was transferred to dialysis tubing (Spectra/Por 32 mm; MWCO 6-8000) and dialyzed against PBS (7×800 mL) at 4–8° over 2 d. The retentate was then 0.22 mm filtered and stored at 4–8°.

Incubation of Macromolecular Prodrugs with Liver Extracts

A solution of Dextran (10 kDa)-CM-EDA-P-araA from Example 41 (6.17 mg/mL, 3.26 mM araA, 1.00 mL) in PBS was mixed with liver extract (1.00 mL). The reaction mixture was incubated at 37°. Controls with conjugate and liver extract only were also incubated at 37° (both diluted 1:1 with PBS). After 60 min, the solutions were cooled to RT and chromatographed using a Waters UHG250 GPC column (300×7.8 mm ID) in a Waters Millennium HPLC System (0.50 mL/min, 20 mM PO$_4$, pH7, 0.1 M NaCl).

Incubation of Macromolecular Prodrug with Human Plasma

A solution of Dextran (10 kDa)-CM-EDA-P-araA from Example 41 (6.17 mg/mL, 3.26 mM araA; 1.00 mL) in PBS was mixed with human plasma (1.00 mL). The reaction mixture was incubated at 37°. After 60 min, the solution were cooled to RT and chromatographed using a Waters UHG250 GPC column (300×7.8 mm ID) in a Waters Millennium HPLC System (0.50 mL/min, 20 mM PO$_4$, pH7, 0.1 M NaCl).

Results

FIG. 5 shows the prodrug is stable in plasma as indicated by the lack of material at the mobilities of araA and araAMP.

FIG. 6 shows the prodrug beaks down readily with a liver extract, as evident by the peaks for araAMP, araXanthosine monophosphate, and araInosine, A small absorbance at the mobility of the prodrug was shown to be the liver extract. Little or no prodrug survived the incubation with liver extract.

Hence, the macromolecular prodrugs of the invention surprisingly have excellent stability in extracellular fluids (plasma), but breakdown readily when exposed to an extract of the intracellular compartment (liver).

We claim:

1. A pharmaceutical composition, comprising:
   a compound having a formula:

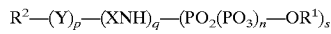

where: $\{PO_2(PO_3)_n-OR^1)_s\}$ is a nucleotide analog; and $R^2$ is a water soluble carrier linked to the nucleotide analog $\{(PO_2(PO_3)_n-OR^1)_s\}$ via an amino-phosphate linkage (NH—PO$_2$), the $R^2$ carrier being selected from the group of polymers, consisting of a synthetic polymer, a non-RME polysaccharide and a modified non-RME polysaccharide, the amino group being provided by a composition including $R^2$, the composition being selected from the group consisting of:
   (a) a formulation wherein $R^2$ has a constituent primary amino group so as to form $R^2$—(PO$_2$(PO$_3$)$_n$—OR$^1$)$_s$ by means of the amino-phosphate linkage such that p=0, q=0, and s≧1;
   (b) a formulation wherein $R^2$ lacks the constituent primary amino group, the primary amino group being provided by means of a linking group (XNH)$_q$ to form $R^2$—(XNH)$_q$—(PO$_2$(PO$_3$)$_n$—OR$^1$)$_s$ where p=0, and q≧s≧1; and
   (c) a formulation wherein $R^2$ lacks the constituent primary amino group, but including a constituent hydroxyl group, the primary amino group being provided by a bridging group (Y)$_p$ for reacting with the hydroxyl group on $R^2$ and the linking group to form $R^2$—(Y)$_p$—(XNH)$_q$—(PO$_2$(PO$_3$)$_n$—OR$^1$)$_s$, such that p≧q≧s≧1.

2. The composition according to claim 1 wherein the OR$^1$ is selected from the group consisting of araA, araC, ddI, AZT, and 5 FUDR, acyclovir, ribavirin, and ganciclovir.

3. The composition according to claim 1 wherein XNH is selected from the group consisting of lysine, polylysine, ornithine, polyornithine and a diamine.

4. A composition according to claim 1 wherein Y is selected from the group consisting of straight chain acyl groups having C$_{2-10}$, an alcohol, and a substituted amide.

5. The composition according to claim 1 wherein $R^2$ is selected from the group consisting of polyvinylamines, polyacrylamides, polyamino acids, polyvinylic polymers, polysaccharides, and combinations thereof.

6. The composition according to claim 5 wherein the polysaccharide is selected from the group consisting of dextran, hydroxyethyl starch, cellulose, pullulan and inulan.

7. The composition according to claim 2 wherein $R^2$ is a polysaccharide selected from the group consisting of dextran, hydroxyethyl starch, cellulose, pullulan and inulan.

8. The composition according to claim 1 wherein $R^2$ is selected from the group consisting of polyvinylpyrollidone, maleic anhydride divinylether (DIVMA), polyvinyl alcohol (PVA), poly(oxyethylene)glycol (PEG), and N-(2-hydroxypropyl)methacrylamide (HPMA).

9. The composition according to claim 1 wherein $R^2$ is a polysaccharide, Y is a carboxymethyl group, and X is ethylene diamine.

10. The composition according to claim 9 wherein the polysaccharide is dextran, OR$^1$ is araA, and n=0.

11. The composition according to claim 9 wherein the polysaccharide is hydroxyethyl starch, OR$^1$ is araC, and n=0.

12. The composition according to claim 1 wherein $R^2$ is a polysaccharide, Y is an isopropyl alcohol group, and X is ethylene diamine.

13. The composition according to claim 12 wherein the polysaccharide is dextran, OR$^1$ is araA, and n=0.

14. The composition according to claim 12, wherein OR$^1$ is araC, n=0, and the polysaccharide is hydroxyethyl starch.

15. A method of endowing a nucleotide analog antiviral agent with substantially enhanced therapeutic efficacy and reduced toxicity, comprising:
   (a) providing a nucleotide analog antiviral agent; and
   (b) conjugating the agent with a polymeric carrier via an amide-phosphate bond, the carrier being selected from the group of polymers, consisting of a synthetic polymer, a non-RME polysaccharide and a modified non-RME polysaccharide, so as to reduce the cytotoxicity of conjugate in comparison to the nucleotide analog antiviral agent alone.

16. A method of treating a viral infection or cancer in a patient, comprising:
   (I) providing a compound having a formula:

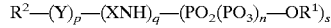

such that $\{PO_2(PO_3)_n-OR^1)_s\}$ is a nucleotide analog; and
   $R^2$ is a water soluble carrier linked to the nucleotide analog $\{(PO_2(PO_3)_n-OR^1)_s\}$ via an amino-phosphate linkage (NH—PO$_2$), the $R^2$ carrier being selected from the group of polymers, consisting of a synthetic polymer, a non-RME polysaccharide and a modified non-RME polysaccharide, the amino group being provided by a composition including $R^2$, the composition being selected from the group consisting of:
   (a) a formulation wherein $R^2$ has a constituent primary amino group so as to form $R^2$—(PO$_2$(PO$_3$)$_n$—OR)$_s$ by means of the amino-phosphate linkage such that p=0, q=0, and s≧1;
   (b) a formulation wherein $R^2$ lacks the constituent primary amino group, the primary amino group being provided by means of a linking group (XNH)$_q$ to form $R^2-(XNH)_q-(PO_2(PO_3)_n-OR^1)_s$ where p=0, and $q \geq s \geq 1$; and (c) a formulation wherein $R^2$ lacks the constituent primary amino group, but including a constituent hydroxyl group, the primary amino group being provided by a bridging group $(Y)_p$ for reacting with the hydroxyl group on $R^2$ and the linking group to form $R^2-(Y)_p-(XNH)_q-(PO_2(PO_3)_n-OR^1)_s$, such that $p \geq q \geq s \geq 1$.

17. The method according to claim 16 wherein the $OR^1$ is selected from the group consisting of araA, araC, ddI, AZT, and 5 FUDR, acyclovir, ribavirin, and ganciclovir.

18. The method according to claim 16 wherein XNH is selected from the group consisting of lysine, polylysine, ornithine, polyornithine and a diamine.

19. A method according to claim 16 wherein Y is selected from the group consisting of straight chain acyl groups having $C_{2-10}$, an alcohol, and a substituted amide.

20. The method according to claim 16 wherein $R^2$ is selected from the group consisting of polyvinylamines, polyacrylamides, polyamino acids, polyvinylic polymers, polysaccharides, and combinations thereof.

21. The composition according to claim 20 wherein the polysaccharide is selected from the group consisting of dextran, hydroxyethyl starch, cellulose, pullulan and inulan.

22. The composition according to claim 19 wherein $R^2$ is a polysaccharide selected from the group consisting of dextran, hydroxyethyl starch, cellulose, pullulan and inulan.

23. The method according to claim 16 wherein $R^2$ is selected from the group consisting of polyvinylpyrollidone, maleic anhydride divinylether (DIVMA), polyvinyl alcohol (PVA), poly(oxyethylene)glycol (PEG), and N-(2-hydroxypropyl)methacrylamide (HPMA).

24. The method according to claim 16 wherein $R^2$ is a polysaccharide, Y is a carboxymethyl group, and X is ethylene diamine.

25. The method according to claim 24 wherein the polysaccharide is dextran, $OR^1$ is araA, and n=0.

26. The method according to claim 24 wherein the polysaccharide is hydroxyethyl starch $OR^1$ is araC, and n=0.

27. The method according to claim 16 wherein $R^2$ is a polysaccharide, Y is an isopropyl alcohol group, and X is ethylene diamine.

28. The method according to claim 27 wherein the polysaccharide is dextran, $OR^1$ is araA, and n=0.

29. The method according to claim 27, wherein $OR^1$ is araC, n=0, and the polysaccharide is hydroxyethyl starch.

* * * * *